United States Patent [19]

Haley et al.

[11] Patent Number: 5,086,060
[45] Date of Patent: Feb. 4, 1992

[54] COMPOUND AND METHOD FOR TREATING SKIN FOR ACNE OR PSORIASIS

[75] Inventors: Neil F. Haley, Fairport; Xina Nair, East Amherst, both of N.Y.; Gerard J. Gendimenico, Hillsborough, N.J.; F. Christopher Zusi, Tonawanda; R. Thomas Swann, Buffalo, both of N.Y.

[73] Assignee: Eastman Kodak Company, Rochester, N.Y.

[21] Appl. No.: 552,726

[22] Filed: Jul. 16, 1990

Related U.S. Application Data

[63] Continuation-in-part of Ser. No. 384,948, Jul. 25, 1989, abandoned.

[51] Int. Cl.$^5$ .................. A61K 31/21; A61K 31/24; C07D 455/06; C07D 277/62; C07F 7/04
[52] U.S. Cl. ........................... 514/294; 546/94; 546/95; 548/160; 548/180; 556/9; 556/407; 556/437; 556/438; 558/414; 558/433; 564/88; 564/169; 564/217; 514/63; 514/367; 514/477; 514/478; 514/490; 514/492; 514/514; 514/520; 514/502; 514/521; 514/522; 514/529; 514/533; 514/859; 514/863
[58] Field of Search ............... 514/294, 367, 478, 490, 514/520, 521, 529, 533, 502, 859, 863, 492; 556/9; 546/95; 558/414, 433; 548/180, 160; 564/88, 169, 217

[56] References Cited

U.S. PATENT DOCUMENTS 4,595,696 6/1986 Loev et al. ............................ 514/513
4,877,805 10/1989 Kligman ................................ 514/381
4,888,342 12/1989 Kligman ................................ 514/419

FOREIGN PATENT DOCUMENTS 906000 9/1962 United Kingdom .

OTHER PUBLICATIONS

Straumfjord, M. D., Acne, pp. 219–225 (1943).
South-East Scotland Faculty of the College of General Practioners, British Medical Journal, p. 294 (1963).
Lynch et al., Archives of Dermatology and Syphilology (1947) pp. 355, 357.
Mitchell et al., Archive of Dermatology and Syphilology (1951) pp. 428–430.
Stüttgen et al., Dermatologica, 124, 65–80 (1962).
Harmes et al., Acta. Derm Venereol (Stockh) 1986, 66, 149–154.
Mezick et al., The Journal of Investigative Dermatology 83, 110–113 (1984).
J. A. D. Anderson et al., Brit. Med. J. 2, 294–296 (1963).
Von. P. Beer, Dermatologics, 124; 192–195 (1962).

*Primary Examiner*—Cecilia Shen
*Attorney, Agent, or Firm*—Betty J. Deaton; J. Jeffrey Hawley

[57] ABSTRACT

The effects of acne and psoriasis are relieved by applying either topically or by oral adminstration, a compound having the structure:

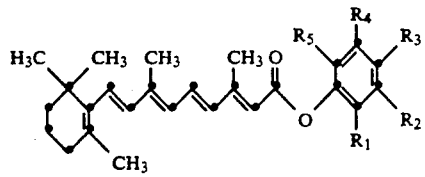

wherein
R$_1$, R$_2$, R$_3$, R$_4$ and R$_5$ are independently selected from the group consisting of H, Cl, straight or branched alkyl of 1 to 10 carbon atoms, NO$_2$, COOR$_6$, CN, OR$_6$, NR$_6$R$_7$, NR$_6$C(=S)NR$_7$R$_8$, NF$_6$COR$_7$, SO$_2$NR$_6$R$_7$, CH(CH$_3$)COOH, CONR$_6$R$_7$, COR$_6$, OCONR$_6$R$_7$, NR$_6$COONR$_7$, R$_9$OR$_6$, NR$_6$SO$_2$R$_7$, Si(CH$_3$)$_3$, and NR$_6$CONR$_7$R$_8$, R$_3$ together with R$_4$ forms a benzo ring or taken together with R$_2$ forms a benzo or tetrahydrobenzo ring or together with R$_2$ and R$_1$ forms a:

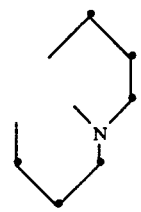

moiety or together with R$_2$ forms a

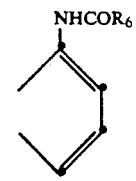

moiety or R$_2$ together with R$_1$ forms a benzo ring or R$_2$ together with R$_3$ forms a

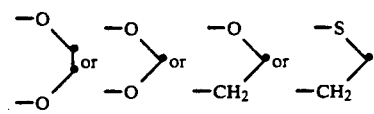

moiety, or
R$_1$ is independently selected from the group consisting of

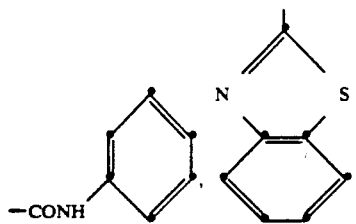

moiety, $R_6$, $R_7$ and $R_8$ are indenpendently selected from the group consisting of straight or branched alkyl containing from 1 to 10 carbon atoms, aryl and containing from 6 to 10 carbon atoms and hydrogen, and $R_9$ is alkylene or 1 to 6 carbon atoms, and iron carbonyl complexes thereof, to an area of the human skin in an amount effective to repair damage due to acne or psoriasis.

This treatment is not accompanied by substantial discomfort or dermatological irritation.

16 Claims, No Drawings

COMPOUND AND METHOD FOR TREATING SKIN FOR ACNE OR PSORIASIS

CROSS-REFERENCE TO RELATED APPLICATIONS

This application is a continuation-in-part of copending U.S. application Ser. No. 384,948 filed on July 25, 1989, now abandoned.

FIELD OF THE INVENTION

This invention relates to a compound and a method of treating skin diseases relating to acne and/or psoriasis by application, either topical or by oral ingestion of specific polyene compositions.

BACKGROUND OF THE INVENTION

Acne is a dermatological disorder which is more prevalent in adolescence and is found mainly within the age group of about 15 to 22. As it occurs primarily in the face and trunk areas, affecting the appearance of the patient, it probably causes more mental pain and anguish to those afflicted than many other diseases which, from a physical standpoint, may be much more severe. The basic lesion of acne is the comedo or "blackhead" of a pilosebaceous follicle. The condition may be mild and transient with only a few blackheads which can easily be ejected by pressure and are of little concern, or may be severe, persistent, and very disfiguring with the more serious cases frequently leaving permanent scarring.

There have been many treatments proposed for acne, almost any treatment giving some relief. What appears to occur in the development of acne is that there is an initial filling up of the follicle with a rather tough, keratinous material. The impactation of horny material is the whitehead and blackhead. As a result of bacterial growth in these horny impactations, the follicle ruptures initiating the inflammatory phase of the disease which takes the form of pustules, papules, cysts and nodules.

One of the commonly used methods for acne treatment is the use of peeling agents which cause exfoliation with the removal of some of the keratinous plugs. In the more serious cases where pustular or cystic lesions exist, the same are evacuated by incision and the contents expressed. Various other therapies have been employed, such as vaccine therapy, to assist in the control of chronic infection and increase the patient's resistance to Staphylococcis; hormone therapy, which is applicable only for female patients who may be put on routine contraceptive regimen with estrogen; antibacterial therapy for the treatment of extensive pustular or cystic acne where the patient may be treated with tetracyclines, penicillin, erythromycin, or other of the antibacterial agents and, in some instances, general surgical skin planing may be used.

The administration of large oral doses of vitamin A has been suggested as being beneficial in acne, Staumford, J. V.: "Vitamin A: Its Effects on Acne," *Northwest Med.*, 42; 219-225, August 1943), although other investigators have felt it to be ineffective (Anderson, J. A. D. et al, "Vitamin A in Acne Vulgaris," *Brit. Med. J.* 2: 294-296, August 1963; Lynch, F. W. et al, "Acne Vulgaris Treated With Vitamin A," *Arc Derm.* 55: 355, 357, March 1947, and Mitchell, G. H. et al, "Results of Treatment of Acne Vulgaris by Intramuscular Injections of Vitamin A," *Arch. Derm.*, 64: 428-430, October 1951).

Vitamin A acid has been applied topically. Beer (Beer, Von P., "Untersuchungen über die Wirkung der Vitamin A-Saure," *Dermatologica*, 124: 192-195, March 1962) and Stüttgen (Stüttgen, G., Zur Lokalbehandlung von Keratosen mit Vitamin A-Saure," *Dermatologica*, 124: 65-80, February 1962) reported achieving good results in those hyperkeratotic disorders which are responsive to high oral doses of Vitamin A. Among those treated by Beer and Stüttgen were patients with acne; however, these investigators reported no effective results on this disorder. British Patent 906,005 discloses a cosmetic peparation containing vitamin A acid for regulation of the cornification processes of human-skin. However, this treatment also results in great irritation to the skin, which severely limits its usefullness.

In U.S. Pat. No. 4,595,696 certain polyenes are described as being useful in treating inflammatory or allergic conditions. These conditions are far afield of acne and materials useful for the treatment of inflammatory conditions are not expected to be useful in the treatment of acne and vice versa.

In addition, it has been reported in "Arotinoid Ro 13-6298 and Etretin: Two New Retinoids Inferior to Isotretinoin in Sebrum Suppression and Acne Treatment", by Harms, M. et al, *Acta Derm Venereol* (Stockh) 1986; 66: 149-154, that extremely close analogs of retinoic acid are not effective in the treatment of acne. This illustrates the unpredictability of these compounds to treat acne.

SUMMARY OF THE INVENTION

The present invention relates to a method of treating acne or psoriasis comprising administering a compound having the structure:

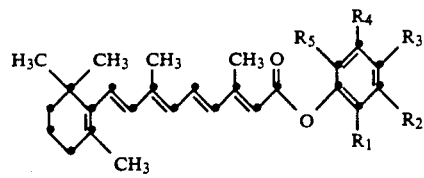

wherein $R_1$, $R_2$, $R_3$, $R_4$ and $R_5$ are independently selected from the group consisting of H, Cl, straight or branched alkyl of 1 to 10 carbon atoms, $NO_2$, $COOR_6$, CN, $OR_6$, $NR_6R_7$, $NR_6C(=S)NR_7R_8$, $NR_6COR_7$, $SO_2NR_6R_7$, $CH(CH_3)COOH$, $CONR_6R_7$, $COR_6$, $OCONR_6R_7$, $NR_6COONR_7$, $R_9OR_6$, $NR_6SO_2R_7$, $Si(CH_3)_3$, and $NR_6CONR_7R_8$, $R_3$ together with $R_4$ forms a benzo ring or taken together with $R_2$ forms a benzo or tetrahydrobenzo ring or together with $R_2$ and $R_1$ forms a:

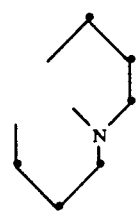

moiety or together with $R_2$ forms a

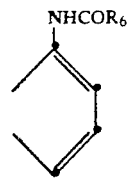

moiety or $R_2$ together with $R_1$ forms a benzo ring or $R_2$ together with $R_3$ forms a

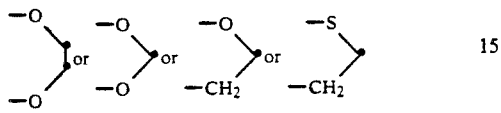

moiety, or $R_1$ is independently selected from the group consisting of

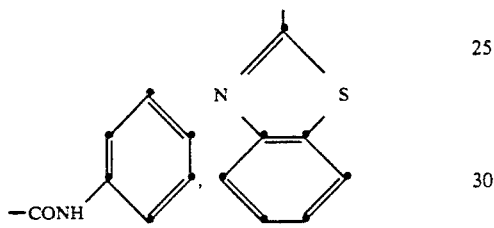

moiety, $R_6$, $R_7$ and $R_8$ are independently selected from the group consisting of straight or branched alkyl containing from 1 to 10 carbon atoms, aryl containing from 6 to 10 carbon atoms and hydrogen, and $R_9$ is alkylene of 1 to 6 carbon atoms, and iron carbonyl complexes thereof, to an area of the human skin in an amount effective to repair damage due to acne or psoriasis.

The present invention also provides novel polyenes within the scope of the foregoing structural formula that are useful for topical treatment of acne or psoriasis. More particularly, the novel polyenes of the present invention have the structure:

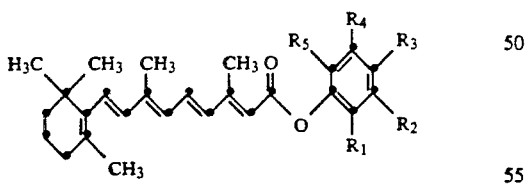

wherein $R_1$, $R_2$, $R_3$, $R_4$ and $R_5$ are independently selected from the group consisting of H, Cl, $NO_2$, CN, $OR_6$, $NR_6C(=S)NR_7R_8$, $SO_2NR_6R_7$, $CH(CH_3)COOH$, $OCONR_6R_7$, $NR_6COONR_7$, $R_9OR_6$, $NR_6SO_2R_7$, $Si(CH_3)_3$, $NR_6CONR_7R_8$, $NR_6COR_7$, with the proviso that where $R_3$ is $NHCOR_7$, and $R_1$ and $R_2$ are hydrogen $R_7$ cannot be methyl, straight or branched alkyl of 1 to 10 carbon atoms, with the proviso where $R_1$ is alkyl, the alkyl cannot contain an acetal, $COOR_6$, with the proviso that where $R_1$ is $COOR_6$, $R_6$ is not hydrogen or methyl, and that where $R_3$ is $COOR_6$, $R_6$ is not ethyl, $NR_6R_7$, with the proviso that where $R_1$ or $R_3$ are $NR_6R_7$, $R_6$ and $R_7$ are not both hydrogen, $CONR_6R_7$, with the proviso that where $R_1$ is $CONR_6R_7$, $R_6$ and $R_7$ are not both hydrogen, and, $COR_6$, with the proviso that where $R_3$ is $COR_6$, $R_6$ is not hydrogen, $R_3$ together with $R_4$ forms a benzo ring or taken together with $R_2$ forms a benzo or tetrahydrobenzo ring or together with $R_2$ and $R_1$ forms a:

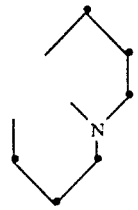

moiety or together with $R_2$ forms a

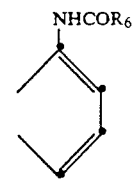

moiety or $R_2$ together with $R_1$ forms a benzo ring or $R_2$ together with $R_3$ forms a

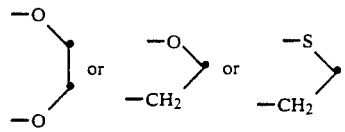

moiety, or $R_1$ is independently selected from the group consisting of

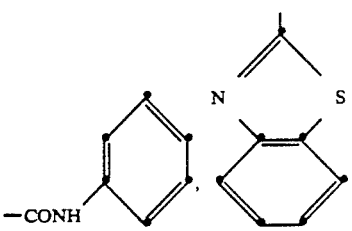

moiety, $R_6$, $R_7$ and $R_8$ are independently selected from the group consisting of straight or branched alkyl containing from 1 to 10 carbon atoms, aryl containing from 6 to 10 carbon atoms and hydrogen, and $R_9$ is alkylene of 1 to 6 carbon atoms, and iron carbonyl complexes thereof.

DETAILED DESCRIPTION OF THE PREFERRED EMBODIMENTS

The treatment of skin with the polyenes of the present invention aid in clearing acne in the skin.

The method of treating acne or psoriasis of this invention comprises administering a compound having the structure:

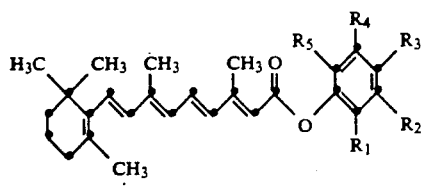

wherein $R_1$, $R_2$, $R_3$, $R_4$ and $R_5$ are independently selected from the group consisting of H, Cl, straight or branched alkyl of 1 to 10 carbon atoms, $NO_2$, $COOR_6$, CN, $OR_6$, $NR_6R_7$, $NR_6C(=S)NR_7R_8$, $NR_6COR_7$, $SO_2NR_6R_7$, $CH(CH_3)COOH$, $CONR_6R_7$, $COR_6$, $OCONR_6R_7$, $NR_6COONR_7$, $R_9OR_6$, $NR_6SO_2R_7$, $Si(CH_3)_3$, and $NR_6CONR_7R_8$, $R_3$ together with $R_4$ forms a benzo ring or taken together with $R_2$ forms a benzo or tetrahydrobenzo ring or together with $R_2$ and $R_1$ forms a:

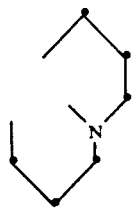

moiety or together with $R_2$ forms a

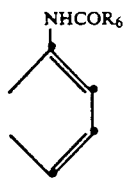

moiety or $R_2$ together with $R_1$ forms a benzo ring or $R_2$ together with $R_3$ forms a

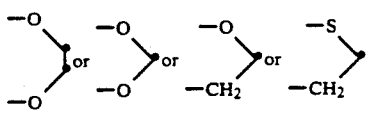

moiety, or $R_1$ is independently selected from the group consisting of

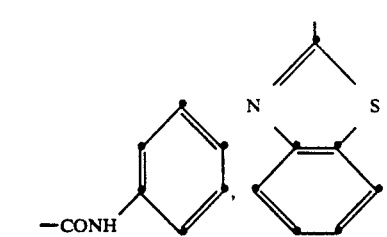

moiety, $R_6$, $R_7$ and $R_8$ are independently selected from the group consisting of straight or branched alkyl containing from 1 to 10 carbon atoms, aryl containing from 6 to 10 carbon atoms and hydrogen.

The novel polyene compounds of the present invention have the structure:

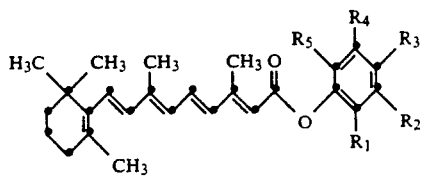

wherein $R_1$, $R_2$, $R_3$, $R_4$ and $R_5$ are independently selected from the group consisting of H, Cl, $NO_2$, CN, $OR_6$, $NR_6C(=S)NR_7R_8$, $SO_2NR_6R_7$, $CH(CH_3)COOH$, $OCONR_6R_7$, $NR_6COONR_7$, $R_9OR_6$, $NR_6SO_2R_7$, $Si(CH_3)_3$, $NR_6CONR_7R_8$, $NR_6COR_7$, with the proviso that where $R_3$ is $NR_6COR_7$, and $R_1$ and $R_2$ are hydrogen $R_7$ cannot be methyl, straight or branched alkyl of 1 to 10 carbon atoms, with the proviso where $R_1$ is alkyl, the alkyl cannot contain an acetal, $COOR_6$, with the proviso that where $R_1$ is $COOR_6$, $R_6$ is not hydrogen or methyl, and that where $R_3$ is $COOR_6$, $R_6$ is not ethyl, $NR_6R_7$, with the proviso that where $R_1$ or $R_3$ are $NR_6R_7$, $R_6$ and $R_7$ are not both hydrogen, $CONR_6R_7$, with the proviso that where $R_1$ is $CONR_6R_7$, $R_6$ and $R_7$ are not both hydrogen, and, $COR_6$, with the proviso that where $R_3$ is $COR_6$, $R_6$ is not hydrogen, $R_3$ together with $R_4$ forms a benzo ring or taken together with $R_2$ forms a benzo or tetrahydrobenzo ring or together with $R_2$ and $R_1$ forms a:

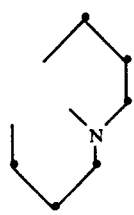

moiety or together with $R_2$ forms a

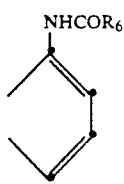

moiety or $R_2$ together with $R_1$ forms a benzo ring or $R_2$ together with $R_3$ forms a

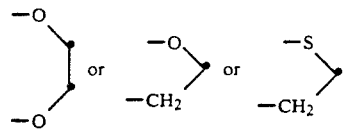

moiety, or
$R_1$ is independently selected from the group consisting of

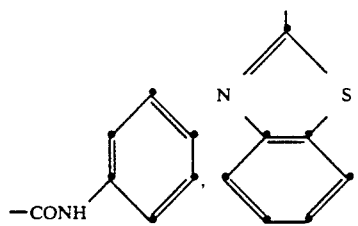

moiety, $R_6$, $R_7$ and $R_8$ are independently selected from the group consisting of straight or branched alkyl containing from 1 to 10 carbon atoms, aryl containing from 6 to 10 carbon atoms and hydrogen, and $R_9$ is alkylene of 1 to 6 carbon atoms, such as methylene, propylene, butylene, trimethylene, etc., and iron carbonyl complexes thereof such as

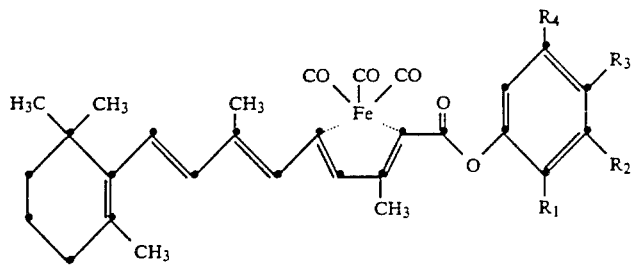

The preferred compounds of the invention include compounds having the above structure and formula wherein $R_2$ and $R_3$ are independently selected from the group consisting of $NR_6COR_7$, $CONR_6R_7$, $SO_2NR_6R_7$, $OCONR_6R_7$, $NR_6COOR_7$, $NR_6CONR_7R_8$, $NR_6SO_2R_7$ and $NR_6C(=S)NR_7R_8$.

For the purposes of this invention, examples of alkyl of 1 to 10 carbon atoms for $R_1$, $R_2$, $R_3$, $R_4$, $R_5$, $R_6$, $R_7$ and $R_8$ are methyl, butyl, pentyl, octyl, ethyl, tertiary-butyl, benzyl, isopropyl, chloroethyl, chloropropyl, hydroxypropyl, carboxyethyl, carboxymethyl, phenynyl, cyanoethyl, and 2-ethylhexyl. Aryl groups containing 6 to 10 carbon atoms as defined in $R_6$, $R_7$, $R_8$ hereinabove are exemplified by phenyl and naphthyl.

The novel polyenes representative of the invention include, but are not limited to Compounds I, III-XXII, XXIV, XXVI-XLIII, and XLV-LII described more fully hereinafter.

The method of preparing these polyenes is well known and is generally described in U.S. Pat. No. 4,595,696 (incorporated herein by reference). Generally, the compounds are formed by reaction of polyene acids with acetic anhydride, boron trifluoride, oxalkylene chloride, phosphorous trichloride, thionyl chloride or a haloformate and then further treated with phenolic compounds.

Polyenes useful for carrying out the present invention include those with the following structures:

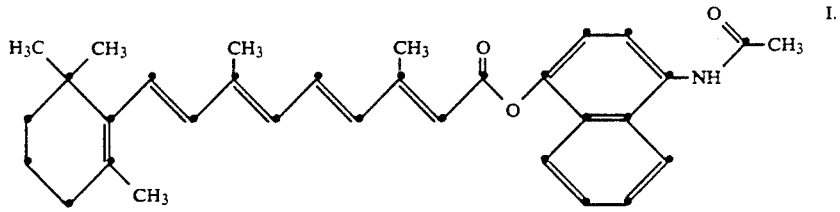

I.

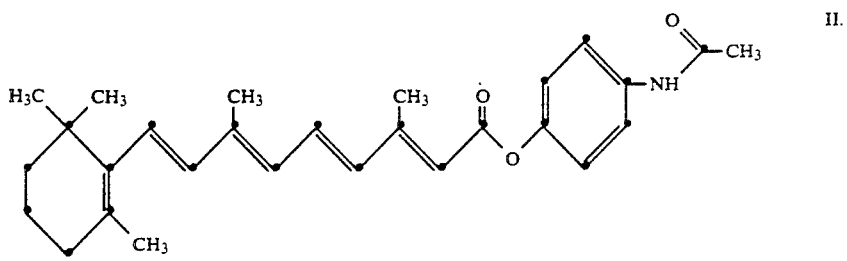

II.

-continued
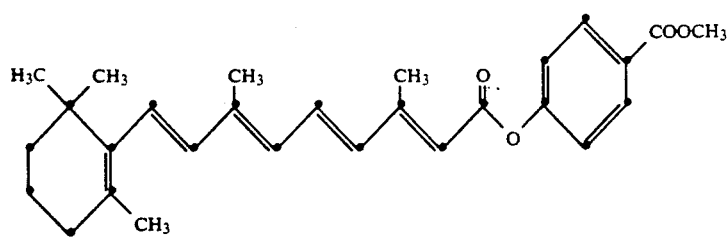
III.
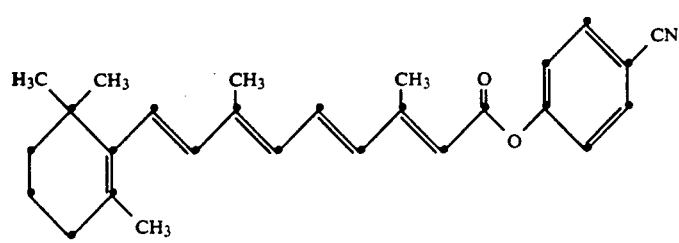
IV.
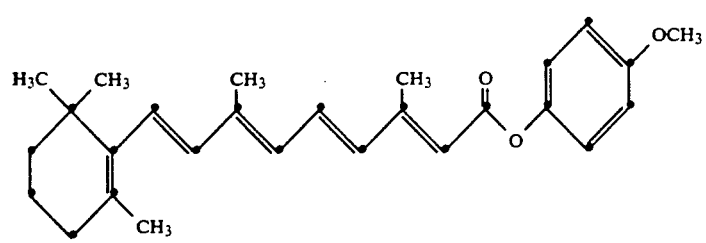
V.
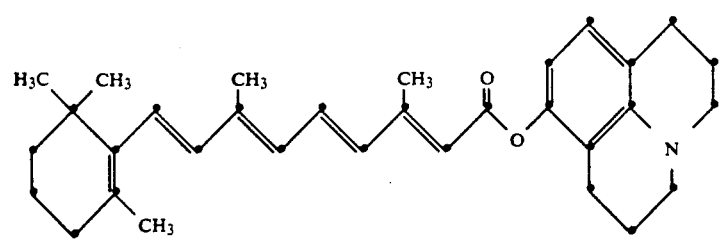
VI.
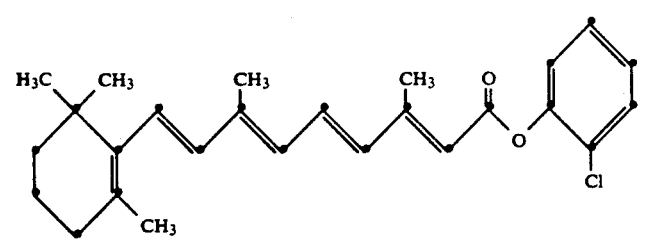
VII.
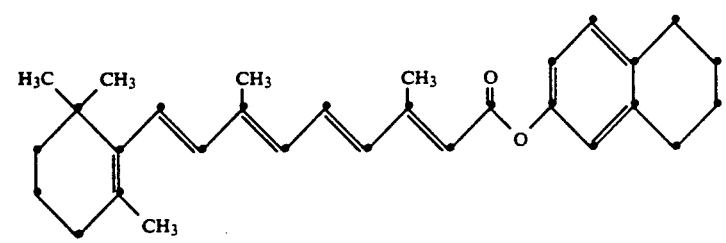
VIII.

-continued
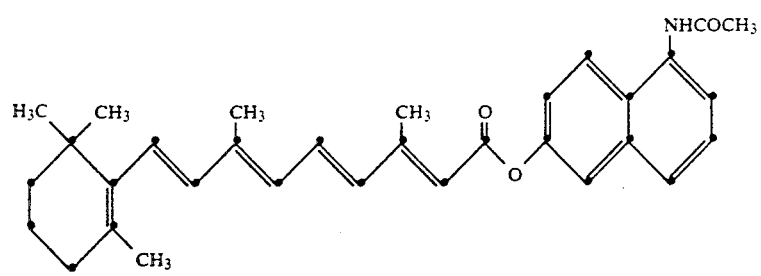 IX.
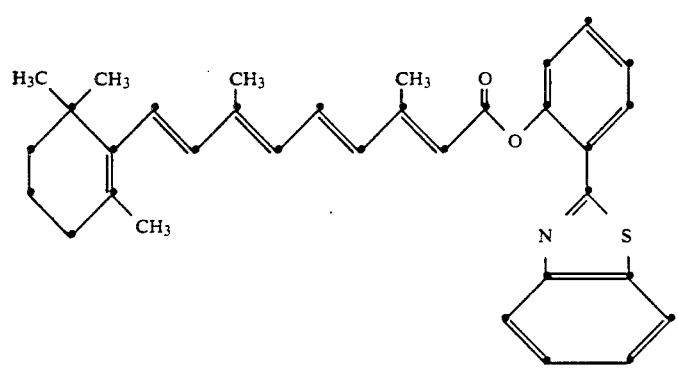 X.
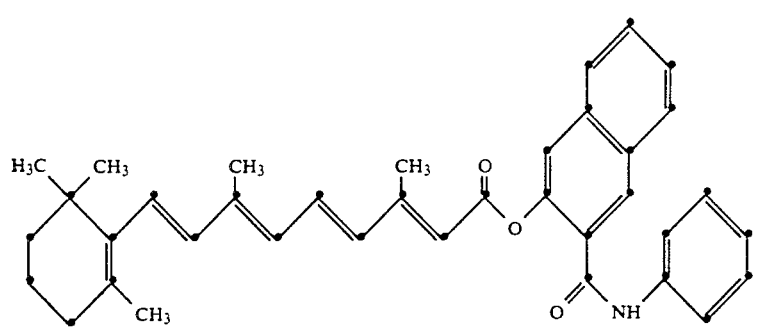 XI.
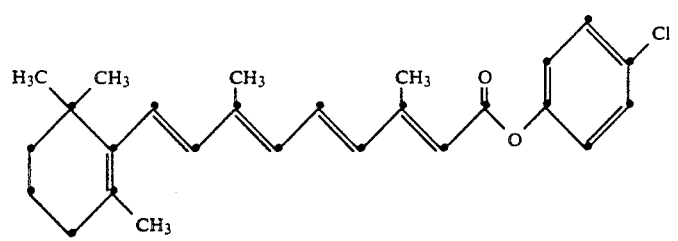 XII.
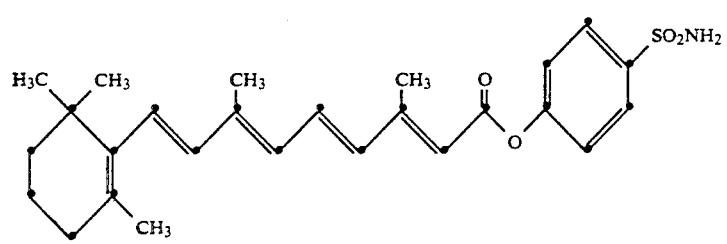 XIII.

-continued
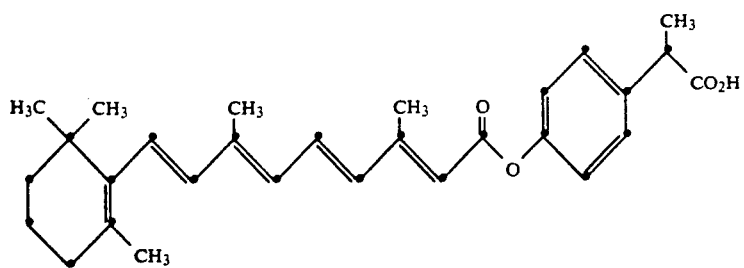
XIV.
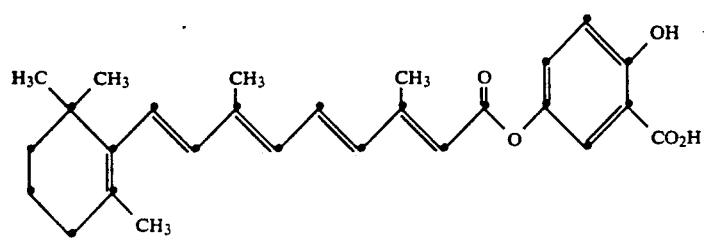
XV.
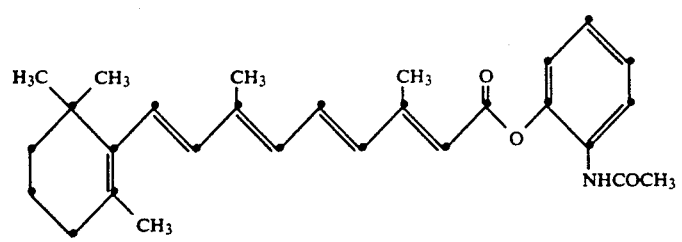
XVI.
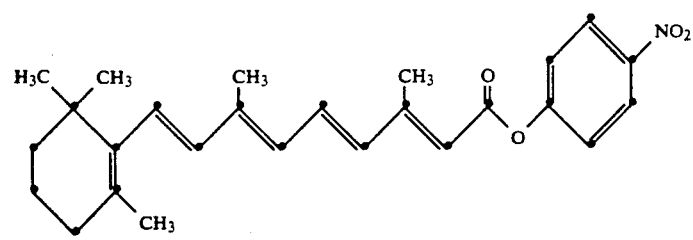
XVII.
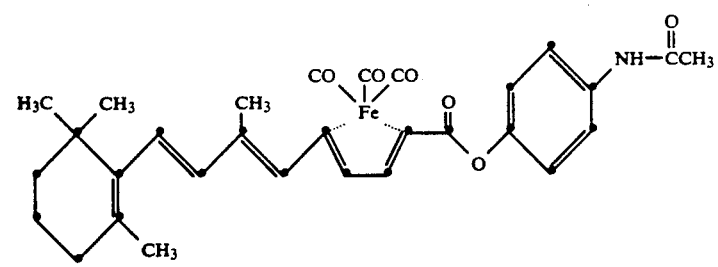
XVIII.
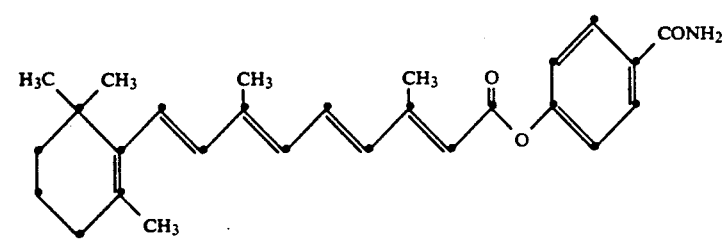
XIX.

-continued
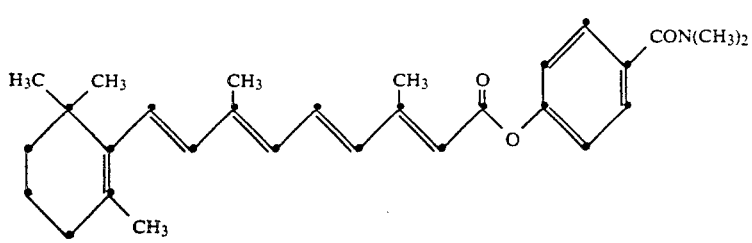 XX.
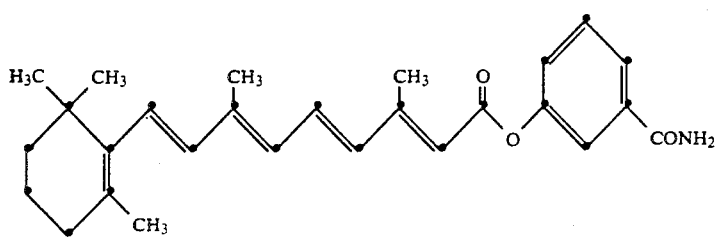 XXI.
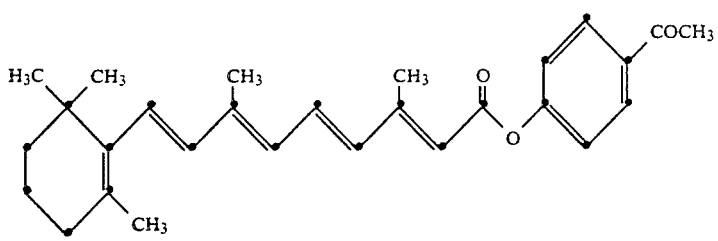 XXII.
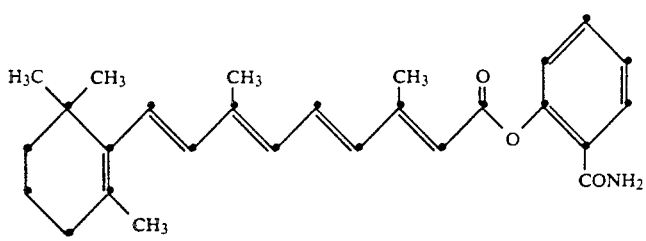 XXIII.
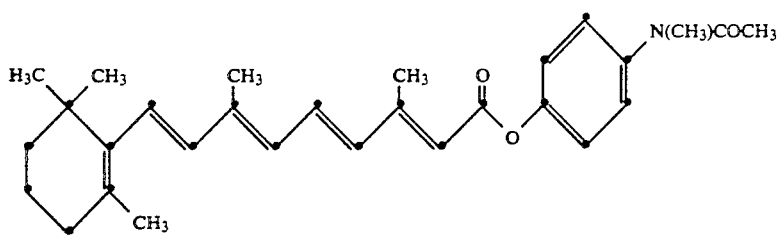 XXIV.
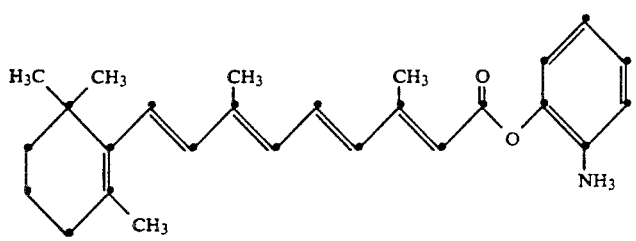 XXV.

-continued
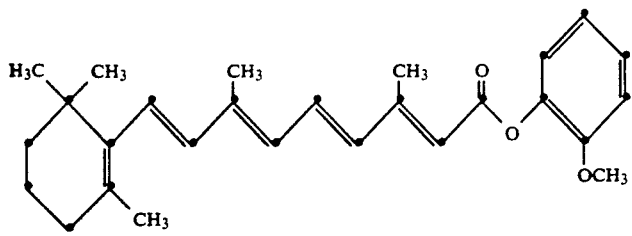
XXVI.
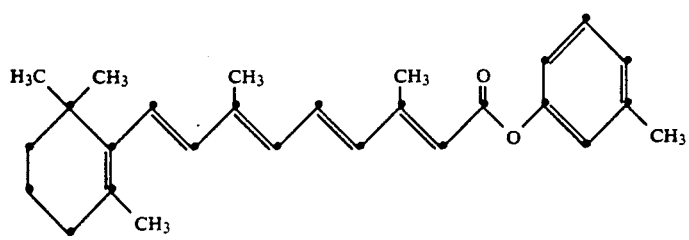
XXVII.
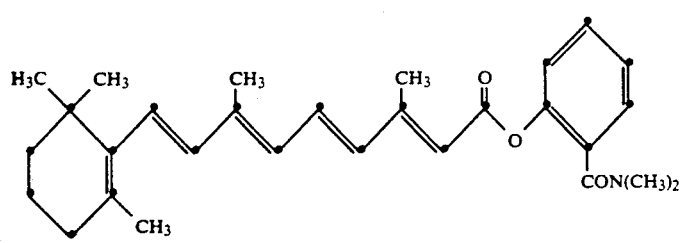
XXVIII.
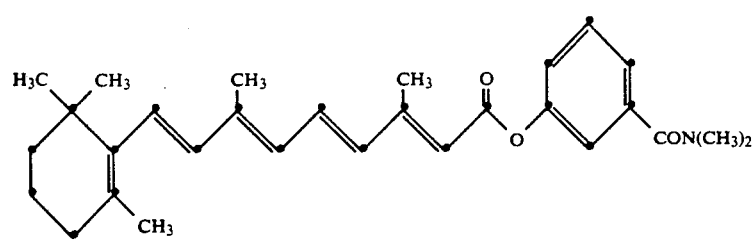
XXIX.
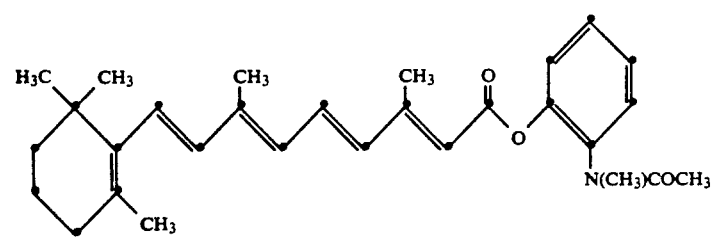
XXX.
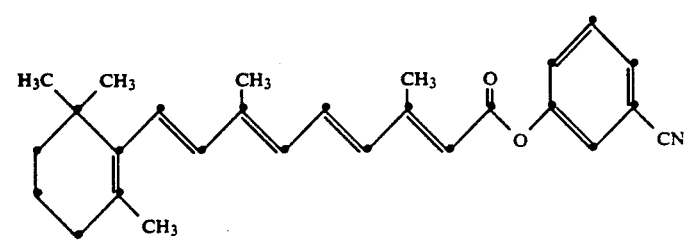
XXXI.

-continued
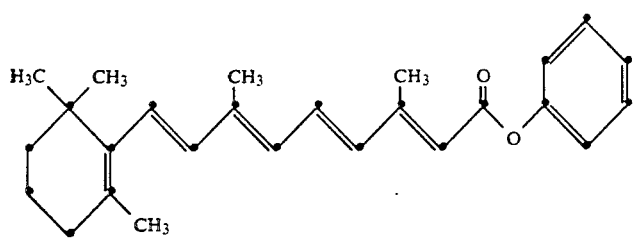
XXXII.
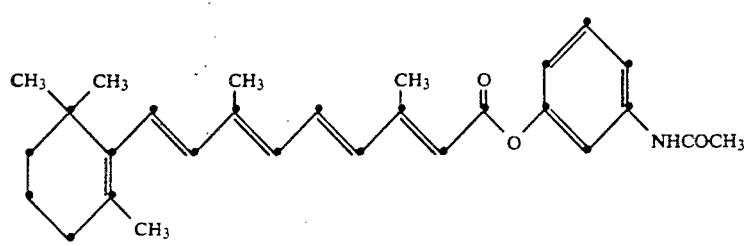
XXXIII.
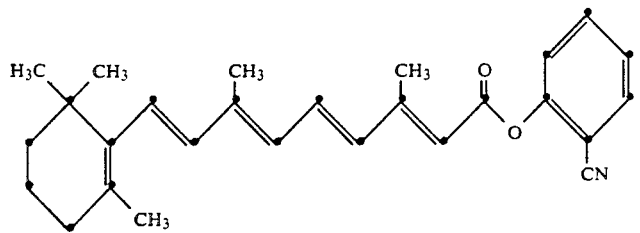
XXXIV.
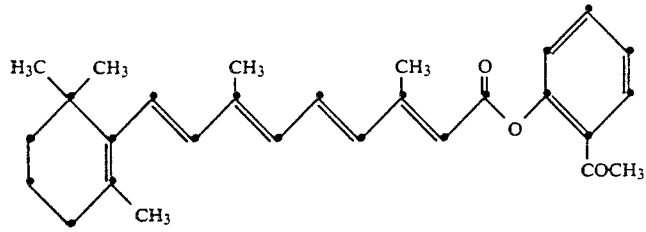
XXXV.
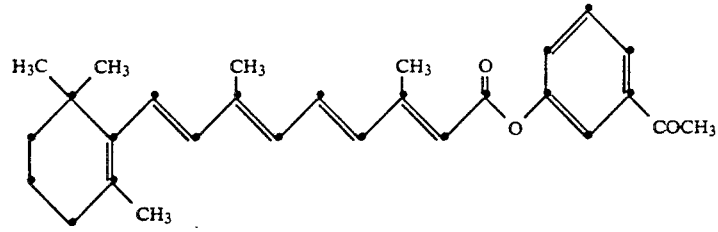
XXXVI.
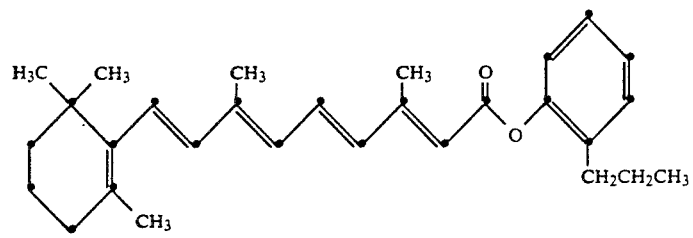
XXXVII.

-continued
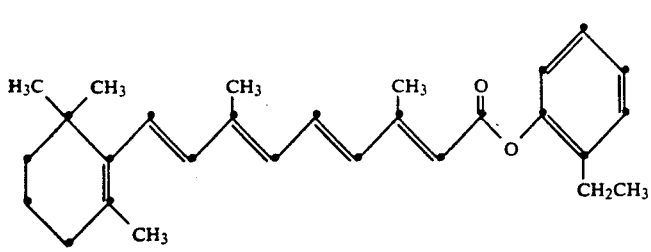
XXXVIII.
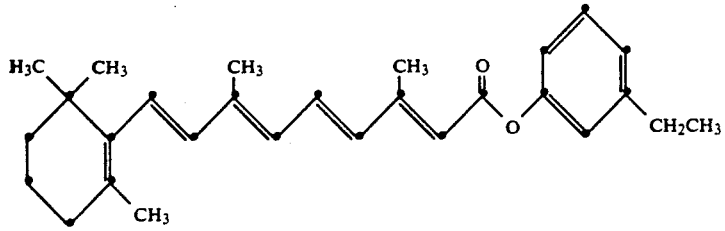
XXXIX.
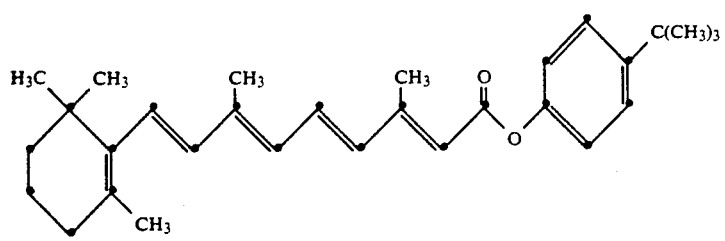
XL.
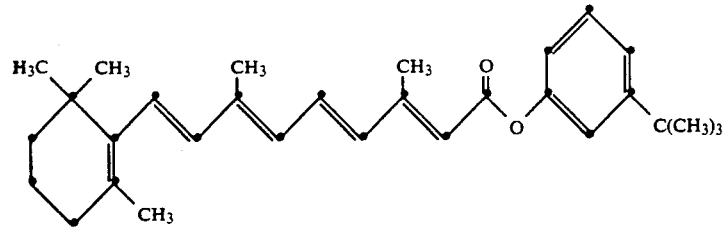
XLI.
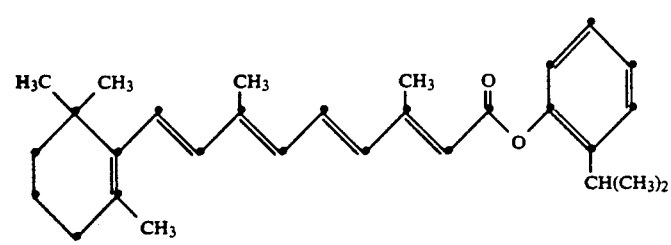
XLII.
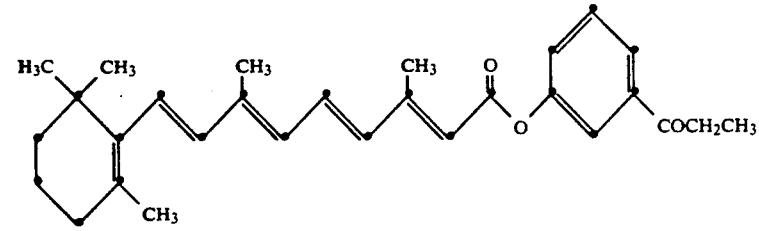
XLIII.

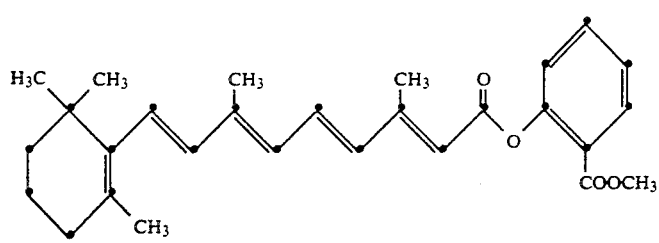
XLIV.
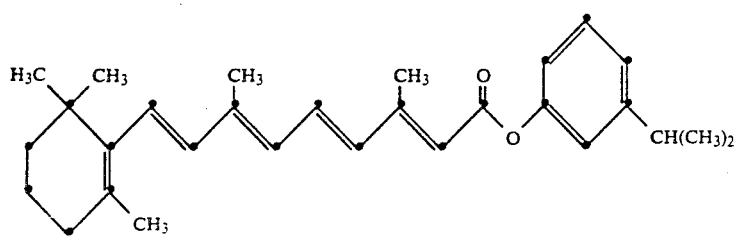
XLV.
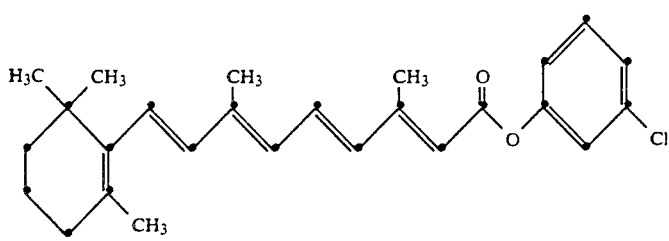
XLVI.
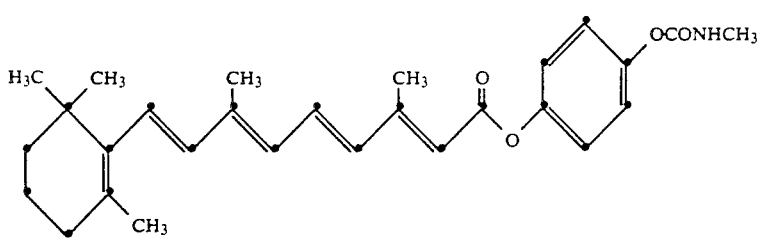
XLVII.
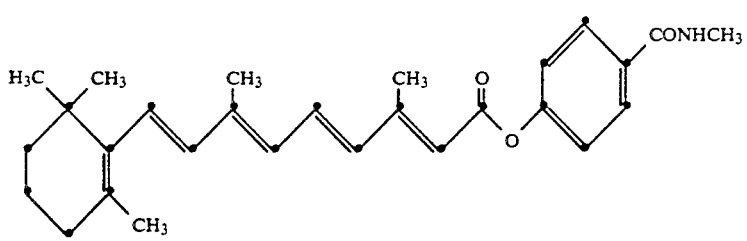
XLVIII.
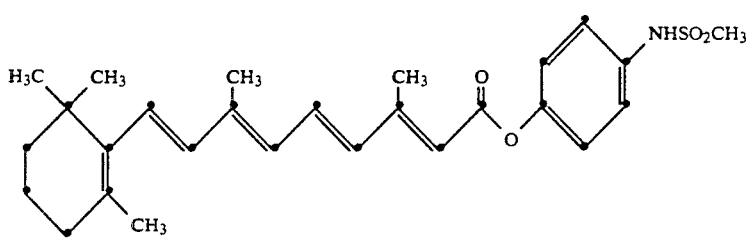
XLIX.

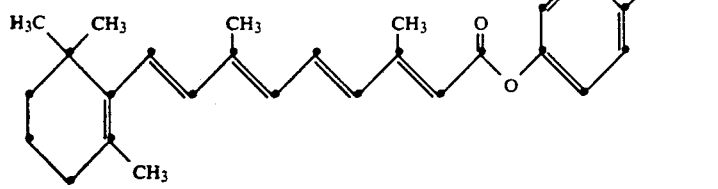

L.

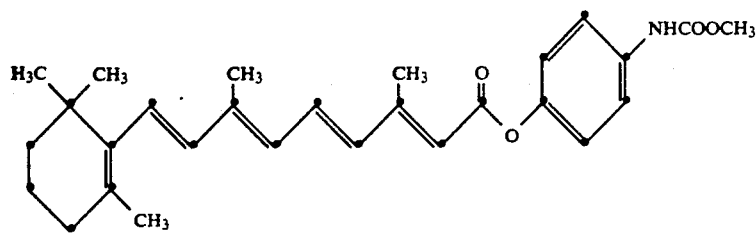

LI.

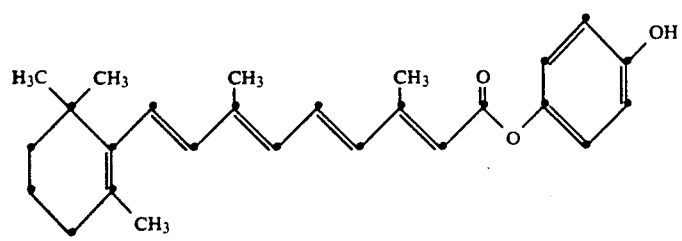

LII.

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk, sugar, certain of clay and so forth. They may be administered orally in the form of solutions which may contain coloring or flavoring agents. When applied topically for treatment of photoaging, they may be provided in the form of dusting powders, aerosol sprays, ointments, aqueous compositions including solutions and suspensions, cream lotions and the like. In this regard, any of the commonly employed extending agents can be used depending on the nature of the product as is well-known in the art.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached.

The polyenes which are formulated in moisturizing bases such as creams or ointments, are usually used in low concentrations. For example, the compounds of the invention may be used in concentrations of about 0.001 percent to 10 percent and preferably about 0.01 percent to 5 percent by weight of the base.

In general, emollient or lubricating vehicles, such as oleaginous substances, which help hydrate the skin are preferred. As used herein, the term "emollient" will be understood to refer to the non-irritating character of the composition as a whole. That is, the nature of the vehicle and amount of polyene therein should be selected so as to provide a sub-irritating dose for topical application. Volatile vehicles which dry or otherwise harm the skin, such as alcohol and acetone, should be avoided.

An ointment base (without water) is preferred in the winter and in subjects with very dry skin. Examples of suitable ointment bases are petrolatum, petrolatum plus volatile silicones, lanolin, and water in oil emulsions, such as Eucerin (Beiersdorf).

In warm weather and often for younger persons, oil in water emulsion (cream) bases, are preferred. Examples of suitable cream bases are Nivea Cream (Beiersdorf), cold cream (USP), Purpose Cream (Johnson & Johnson), hydrophilic ointment (USP), and Lubriderm (Warner-Lambert).

These topical compositions can contain any of the conventional excipients and additives commonly used in preparing topical compositions. Among the conventional additives or excipients which can be utilized in preparing these cosmetic compositions in accordance with this invention are preservatives, thickeners, perfumes and the like. In addition, the conventional antioxidants, such as butylated hydroxyanisoles (BHA), ascorbyl palmitate, propyl gallate, citric acid butylated hydroxy toluene (BHT), ethoxyquin and the like can be incorporated into these compositions. These topical compositions can contain conventional acceptable carriers for topical applications which are generally utilized in these compositions. These compositions may contain thickening agents, humectants, emulsifying agents and viscosity stabilizers, such as those generally utilized. In addition, these compositions can contain flavoring agents, colorants, and perfume which are conventional in preparing cosmetic compositions.

The polyenes can be applied daily until the desired relief is obtained, and this may require one or two (or possibly three) applications each day, depending upon the particular individual. Normally the treatment requires at least a month. Thus, acne in its mildest form (only a small number of comedones) may be substantially cleared in four to six weeks. However, more severe cases may require three months or longer.

This invention is further illustrated by the following examples, which are illustrative only.

EXAMPLE 1

Preparation of p-Acetamidophenyl Retinoate (Compound II)

Retinoic acid (0.010 mole) is dissolved in anhydrous tetrahydrofuran (75 ml) and treated at room temperature with triethylamine (0.011 mol). The solution is stirred for 5 minutes and ethyl chlorformate (0.011 mol) dissolved in anhydrous tetrahydrofuran (20 ml) is added dropwise with stirring. After one hour at room temperature, TLC (Silica gel/Pet ether/ether 3:10 shows only one spot with Rf=0.8 (the carbonic anhydride of retinoic acid). Pentane (100 ml) is added and the triethylamine hydrochloride is collected by filtration. The filtrate is evaporated under vacuum (rotary evaporator) and the residual yellow oil is dissolved in anhydrous acetonitrile (75 ml). Acetamidophenol (0.010 mole) is added in one portion and the mixture is warmed to obtain a solution ($\approx$30° C.). Triethylamine (0.011 mole) is added in one portion followed by 4-dimethylaminopyridine (100 mg). The reaction becomes exothermic and carbon dioxide is evolved. It is stirred at 50° C. for one hour then the yellow solid collected and air dried. Yield 92%, m.p. 200°–202° C. TLC on silica gel shows one spot at origin eluting with 3:1 pet/ether and Rf=0.3 redeveloping with ether alone. The product is recrystallized from acetonitrile. If the product does not crystallize from the acetonitrile reaction mixture, evaporate to an oil and crystallize from mixtures of ethanol-water.

Compounds III–XI, XVII, XIX–LII were prepared by analogous synthetic routes.

The intermediate carbonyl anhydride of the example has the structure

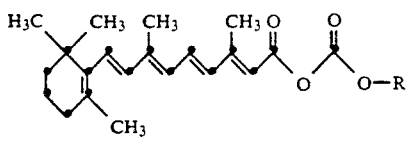

wherein

R is —$C_2H_5$.

The following analytical data found and calculated for compounds II–XI, XVII, XIX, XXI, XXIII, XXXI, XXXII, XXXIII, XXXIV, XLIV and XLVI are as follows:

| Compound | FOUND | | | | CALCULATED | | | |
|---|---|---|---|---|---|---|---|---|
| | C | H | N | Cl | C | H | N | Cl |
| II | 77.3 | 7.8 | 3.0 | | 77.6 | 8.1 | 3.2 | |
| III | 77.4 | 7.9 | | | 77.4 | 7.9 | | |
| IV | 76.0 | 7.8 | 3.2 | | 80.8 | 7.8 | 3.5 | |
| V | 79.9 | 8.4 | | | 79.8 | 8.4 | | |
| VI | 81.1 | 8.8 | 3.0 | | 81.5 | 8.8 | 3.0 | |
| VII | 75.7 | 7.5 | | | 76.0 | 7.6 | | |
| VIII | 81.8 | 8.7 | | | 83.7 | 8.9 | | |
| IX | 77.2 | 7.6 | 3.0 | | 79.5 | 7.7 | 2.9 | |
| X | 77.7 | 6.9 | 2.8 | | 77.8 | 6.9 | 2.8 | |

| Compound | FOUND | | | | CALCULATED | | | |
|---|---|---|---|---|---|---|---|---|
| | C | H | N | Cl | C | H | N | Cl |
| XI | 79.8 | 6.7 | 2.4 | | 81.4 | 7.2 | 2.6 | |
| XVII | 74.0 | 7.4 | 3.1 | | 74.1 | 7.4 | 3.3 | |
| XXIII | 77.06 | 8.00 | 3.33 | | 77.29 | 7.93 | 3.34 | |
| XIX | 77.05 | 7.92 | 3.30 | | 77.29 | 7.93 | 3.34 | |
| XXXI | 80.52 | 7.85 | 3.48 | | 80.76 | 7.78 | 3.49 | |
| XXXII | 82.69 | 8.58 | — | | 82.74 | 8.57 | — | |
| XXI | 76.47 | 8.55 | 3.13 | | 77.29 | 7.93 | 3.34 | |
| XXXIII | 76.88 | 8.17 | 3.22 | | 77.56 | 8.14 | 3.23 | |
| XXXIV | 80.61 | 7.83 | 3.44 | | 80.76 | 7.78 | 3.49 | |
| XLIV | 76.44 | 7.77 | | | 76.74 | 8.11 | — | |
| XLVI | 75.85 | 7.63 | | 8.67 | 75.48 | 7.60 | — | 8.63 |

EXAMPLE 2

Effect of Compounds on Rhino Mouse Utriculi Diameter

In the rhino mouse test, polyene compounds related to Vitamin A, including all-trans retinoic acid, are highly effective in reducing the size of horn-filled utricles in hairless mouse skin (Mezick et al, "Topical and Systemic Effects of Retinoids on Horn-Filled Utriculus Size in the Rhino Mouse. A Model to Quantify 'Antikeratinizing' Effects of Retinoids", *J. Invest. Dermatol.*, 1984; 83:110–113). Hairless rhino mice hr$^{rh}$hr$^{rh}$) were treated with 0.05 ml of Compounds I–XIV, all-trans retinoic acid or the ethanol vehicle on the dorsolateral skin once daily on five consecutive days for one week. Mice were sacrificed by $CO_2$ asphyxiation on the third day after the last treatments. A ⅛" full thickness punch biopsy of skin was removed and placed in a 0.5 percent acetic acid overnight at 4° C. The following day, epidermal sheets were removed from the dermis by peeling with a metal spatula. These sheets were fixed in formalin, dehydrated with ethanol, and kept in xylene.

To assess utricle diameter, each epidermal sheet was placed on a glass slide in a few drops of xylene. The diameter of 20 utricles was measured with an image analyzer. The effect of Compounds I–XIV and all-trans retinoic acid on utriculi diameter is shown in Table 1.

The dose-related response in the rhino mouse test of selected compounds is shown in Table 2. The $ED_{30}$ values shown were calculated by interpolation of the regression lines of the log concentration-percent reduction plots.

TABLE 1

The Effect of Compounds on Rhino Mouse Utriculi Diameter

| Compound | Concentration Percent (W/V) in Ethanol | Utriculi Reduction vs. Ethanol (Percent) |
|---|---|---|
| I | 0.1 | Not Done |
| II | 0.1 | 48 |
| III | 0.1 | 51 |
| IV | 0.1 | 55 |
| V | 0.1 | 43 |
| VI | 0.1 | 45 |
| VII | 0.1 | 48 |
| VIII | 0.1 | 56 |
| IX | 0.16 | 52 |
| X | 0.1 | 9 |
| XI | 0.17 | 44 |
| XII | 0.1 | 44 |
| XIII | 0.1 | 43 |
| XIV | 0.1 | 41 |
| trans-Retinoic Acid | 0.01 | 52 |

TABLE 2

Dose-Related Activity of Selected Compounds and All-Trans Retinoic Acid on Rhino Mouse Utriculi Diameter

| Compound | Concentration Percent (W/V) in Ethanol | Utriculi Diameter Reduction (Percent) | $ED_{30}$ (mM) | Global Irritation |
|---|---|---|---|---|
| Part I | | | | |
| II | 0.01 | 50 | 0.03 | |
|  | 0.001 | 38 | | |
|  | 0.0001 | 6 | | |
| III | 0.1 | 51 | 0.14 | |
|  | 0.01 | 43 | | |
|  | 0.001 | 10 | | |
| IV | 0.1 | 55 | 0.13 | |
|  | 0.01 | 44 | | |
|  | 0.001 | 10 | | |
| V | 0.1 | 43 | 0.12 | |
|  | 0.01 | 36 | | |
|  | 0.001 | 21 | | |
| VI | 0.1 | 45 | 0.56 | |
|  | 0.01 | 14 | | |
|  | 0.001 | 6 | | |
| VII | 0.1 | 48 | 0.20 | |
|  | 0.01 | 30 | | |
|  | 0.001 | 16 | | |
| VIII | 0.1 | 56 | 0.27 | |
|  | 0.01 | 26 | | |
|  | 0.001 | 2 | | |
| trans-Retinoic Acid | 0.1 | 52 | 0.020 | |
|  | 0.01 | 37 | | |
|  | 0.001 | 18 | | |
| Part II | | | | |
| II | 0.1 | | 0.037 | 1.65 |
| XIX | 0.1 | | 0.120 | 2.5 |
| XX | 0.1 | | 0.074 | 4.5 |
| XXI | 0.1 | | 0.074 | |
| XXII | 0.1 | | 0.048 | |
| XXIII | 0.1 | | 0.159 | |
| XXIV | 0.1 | | 0.249 | |
| XXV | 0.1 | | 0.229 | 3.3 |
| XXVI | 0.1 | | 0.393 | 3.3 |
| XXVII | 0.1 | | 0.310 | 6.6 |
| XXVIII | 0.1 | | 0.275 | 6.6 |
| XXIX | 0.1 | | 0.239 | |
| XXX | 0.1 | | 0.229 | |
| XXXI | 0.1 | | 0.131 | 7.3 |
| XXXII | 0.1 | | 0.338 | |
| XXXIII | 0.1 | | 0.196 | |
| trans-Retinoic Acid | 0.1 | | 0.015 | 6.6 |

For the purposes of this invention, Global Irritation score is defined as the sum of erythema, edema and scaling scores. A description of erythema, edema and scaling scores for Compound II is described as follows:

A rabbit model of skin irritation was used to assess the dermatitis produced by treatment with Compound II and all-trans retinoic acid. The rabbit is commonly used as a skin irritation model for predicting the potential local irritation of topically applied materials.

New Zealand albino rabbits, from Beckens Farms, Sanborn, NY, were clipped closely at four sites on the back with an electric hair clipper to give 4 cm×4 cm square sites. Each rabbit received 0.2 ml of Compound II and all-trans retinoic acid, once daily for fourteen consecutive days. Each day, the degree of erythema, scaling and edema was assessed visually by using the Draize 0 to 4 grading method. The results were expressed as average daily Draize score, which was derived by taking the cumulative score over fourteen days, for each parameter, and dividing by fourteen.

This procedure was followed to obtain the Global Irritation scores provided above.

The invention has been described in detail with particular reference to preferred embodiments thereof, but it will be understood that variations and modifications can be effected within the spirit and scope of the invention.

What is claimed is:

1. A method of treating acne or psoriasis comprising administering a compound having the structure:

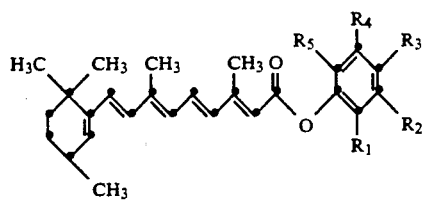

wherein any three of $R_1$, $R_2$, $R_3$, $R_4$ and $R_5$ are independently selected from the group consisting of H, Cl, straight or branched alkyl of 1 to 10 carbon atoms, $NO_2$, $COOR_6$, CN, $OR_6$, $NR_6R_7$, $NR_6C(=S)NR_7R_8$, $NR_6COR_7$, $SO_2NR_6R_7$, $CH(CH_3)COOH$, $CONR_6R_7$, $COR_6$, $OCONR_6R_7$, $NR_6COONR_7$, $R_9OR_6$, $NR_6SO_2R_7$, $Si(CH_3)_3$, and $NR_6CONR_7R_8$.

$R_3$ together with $R_4$ forms a benzo ring or taken together with $R_2$ forms a benzo or tetrahydrobenzo ring or together with $R_2$ and $R_1$ forms a:

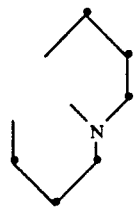

moiety or together with $R_2$ forms a

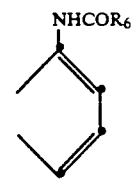

moiety or $R_2$ together with $R_1$ forms a benzo ring,

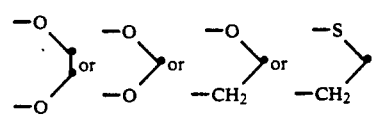

or $R_1$ is independently selected from the group consisting of

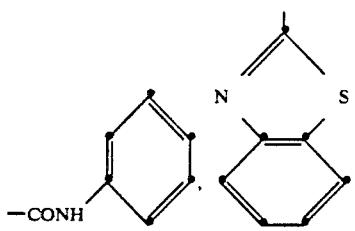

moiety, $R_6$, $R_7$ and $R_8$ are independently selected from the group consisting of straight or branched alkyl containing from 1 to 10 carbon atoms, aryl containing from 6 to 10 carbon atoms and hydrogen, and $R_9$ is alkylene of 1 to 6 carbon atoms, and iron carbonyl complexes thereof, to an area of the human skin in an amount effective to repair damage due to acne or psoriasis.

2. The method of claim 1 wherein $R_2$ and $R_3$ are independently selected from the group consisting of $NR_6COR_7$, $CONR_6R_7$, $SO_2NR_6R_7$, $OCONR_6R_7$, $NR_6COOR_7$, $NR_6CONR_7R_8$, $NR_6SO_2R_7$ and $NR_6C(=S)NR_7R_8$.

3. The method of claim 1 wherein the compound is mixed with a therapeutically and pharmaceutically acceptable carrier material.

4. The method of claim 1 wherein the compound is applied topically.

5. The method of claim 1 wherein the compound is applied by oral administration.

6. The method of claim 1 wherein $R_3$ is $NHCOCH_3$ and $R_1$, $R_2$ and $R_4$ are H.

7. The method of claim 1 wherein the compound comprises about 0.001 percent to about 10 percent by weight of the mixture applied.

8. The method of claim 1 wherein the compound comprises about 0.01 percent to about 5 percent by weight of the mixture applied.

9. The method of claim 3 wherein the compound is applied to human skin.

10. A method of treating acne or psoriasis comprising administering a compound having the structure:

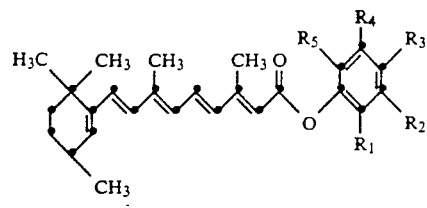

wherein $R^3$ is $NHCOCH_3$ and $R_1$, $R_2$ and $R_4$ are H.

11. A method of treating acne or psoriasis comprising administering a compound having the structure:

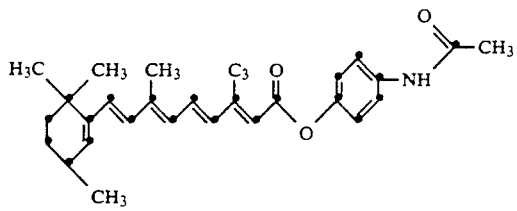

12. The method of claim 1 wherein the compound is selected from the group consisting of

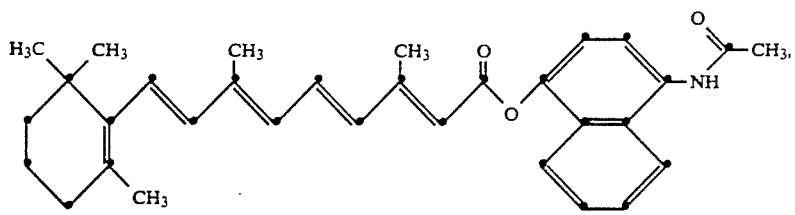

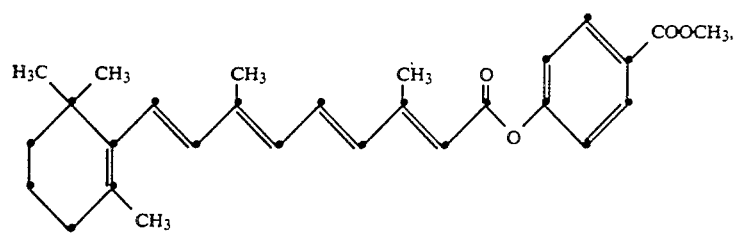

-continued
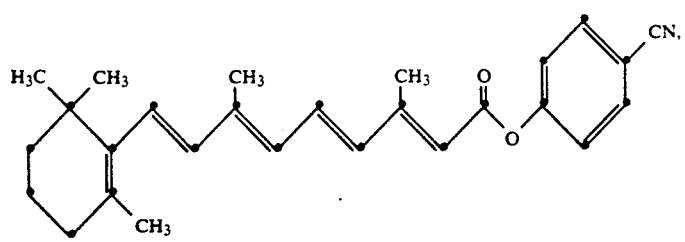
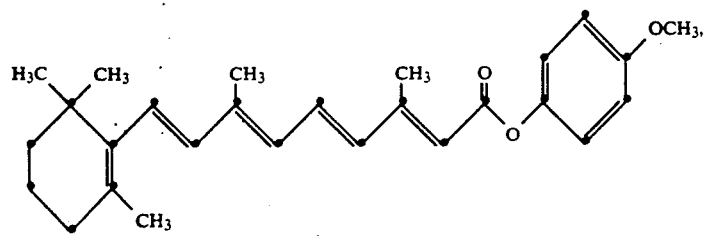
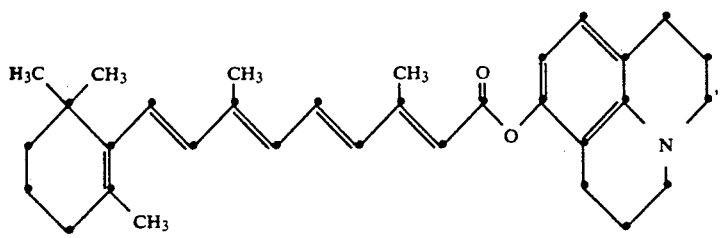
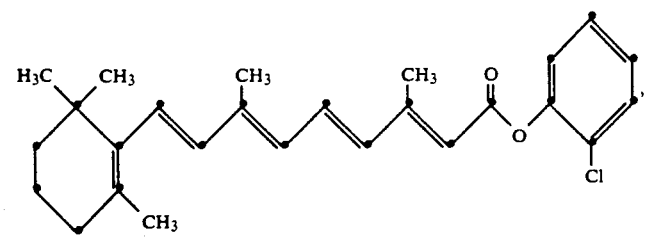
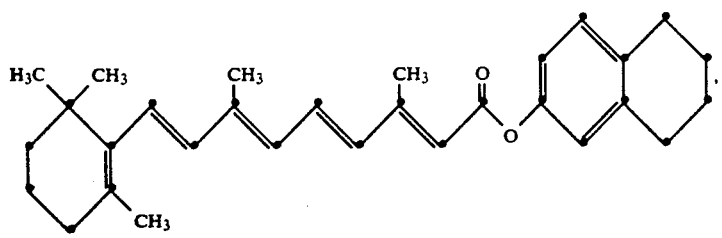
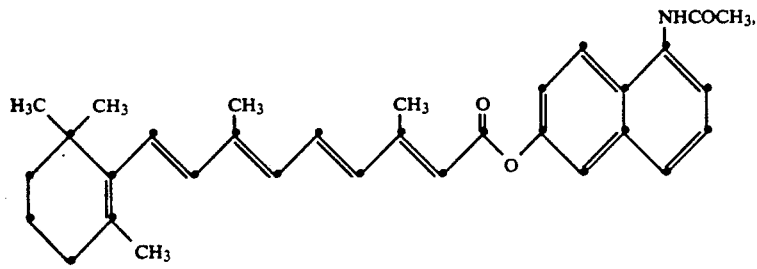

-continued
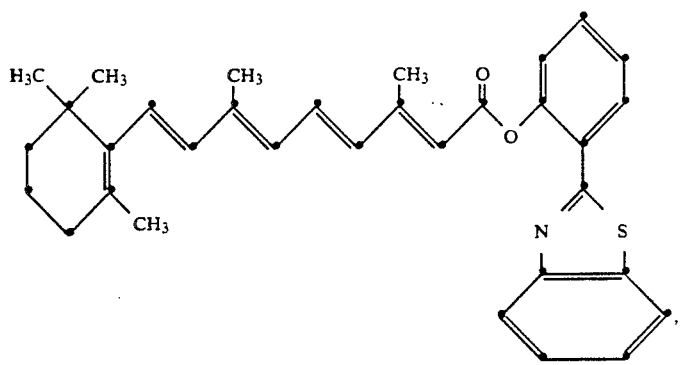
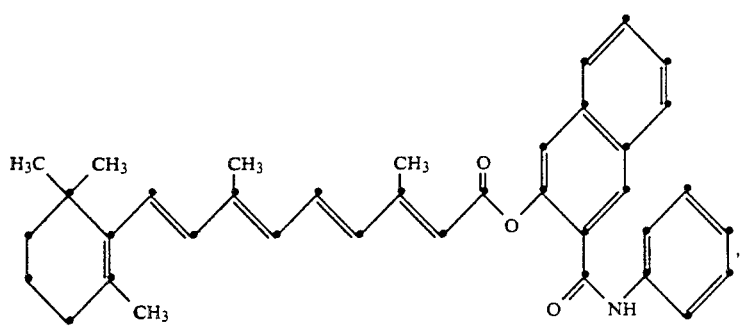
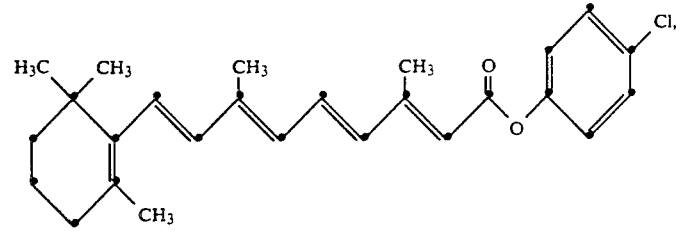
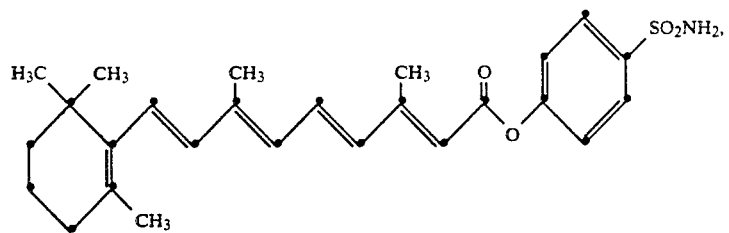
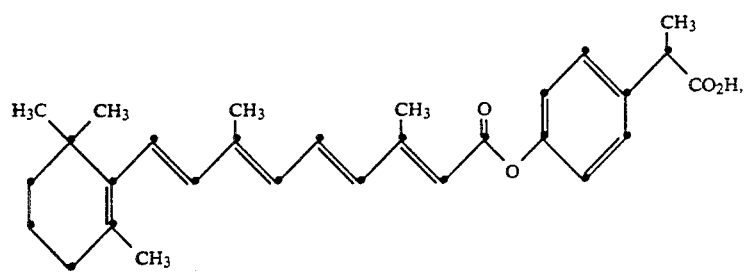

-continued
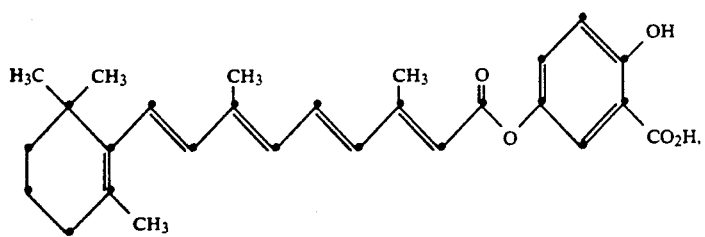
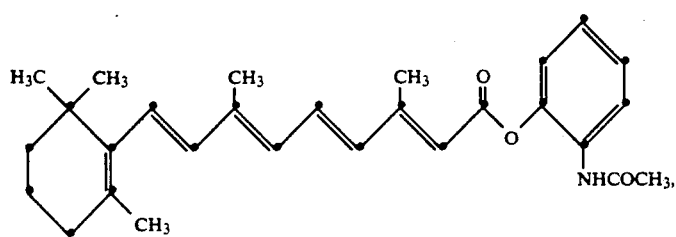
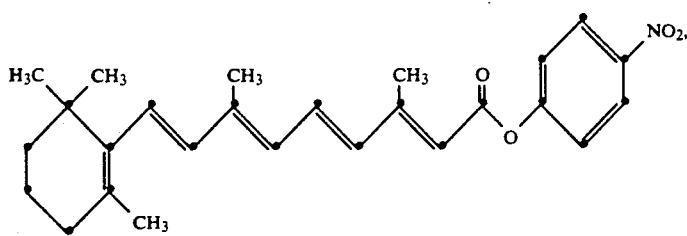
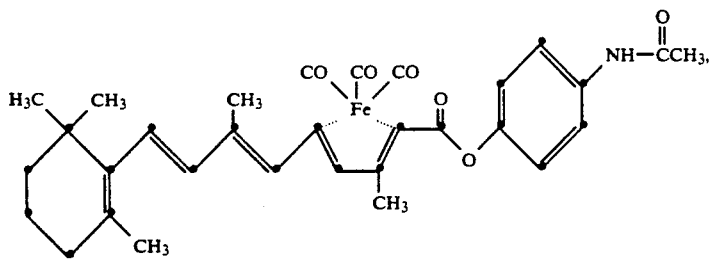
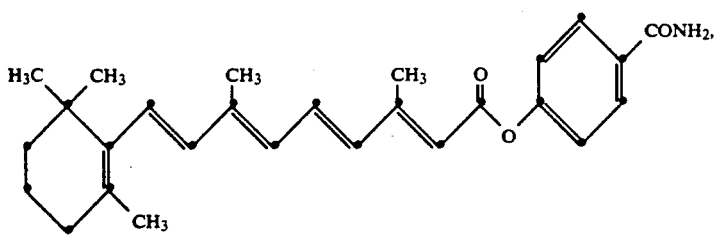
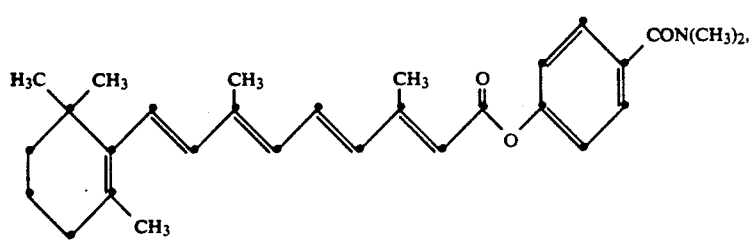

-continued
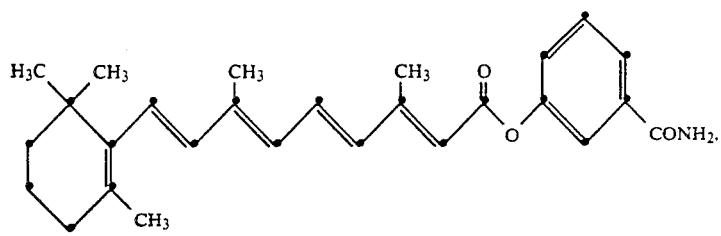
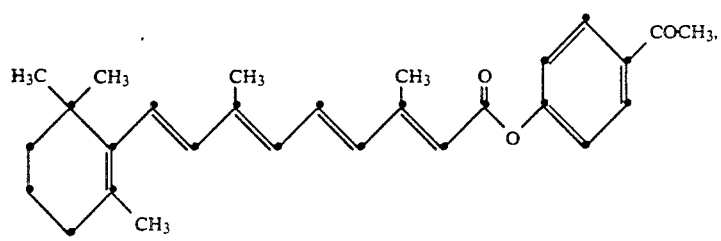
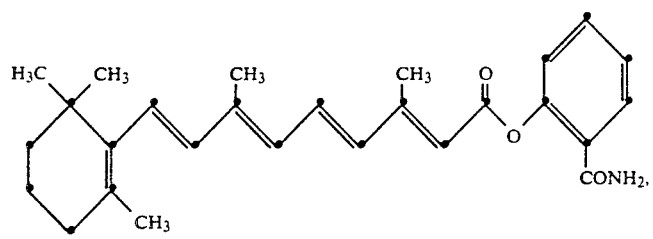
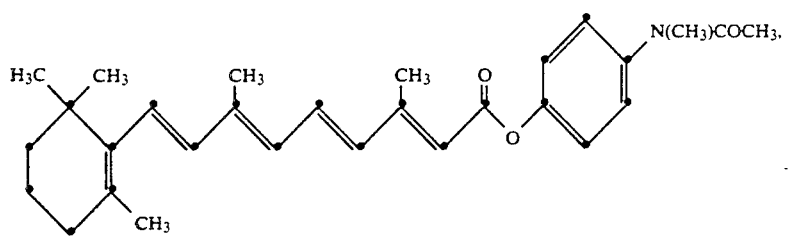
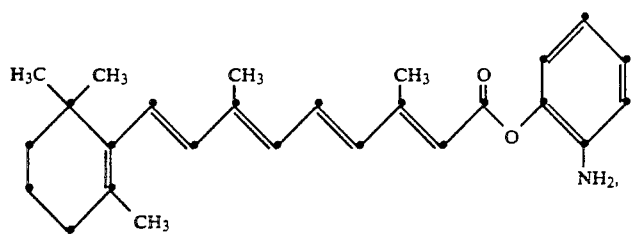
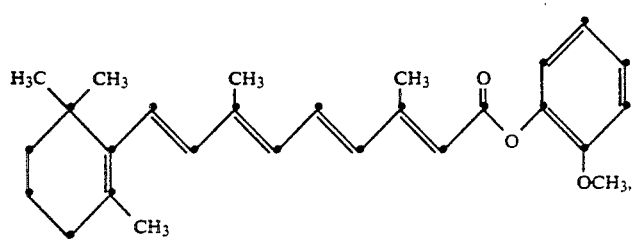

-continued
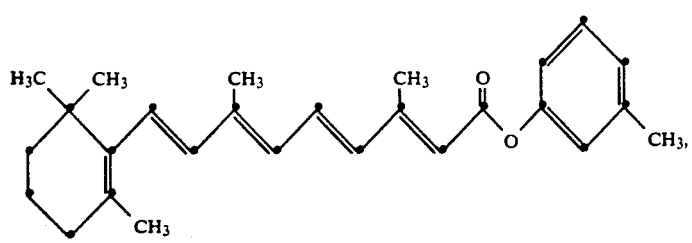
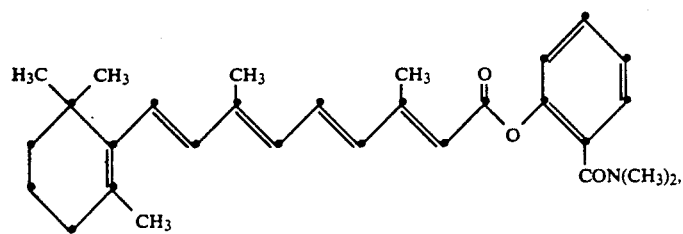
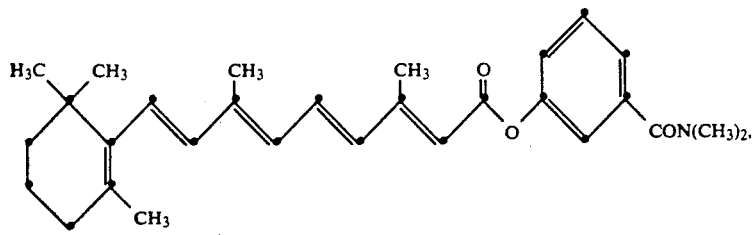
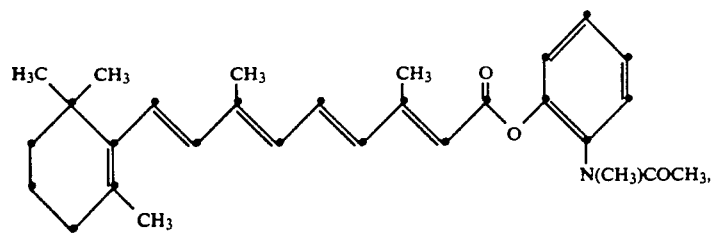
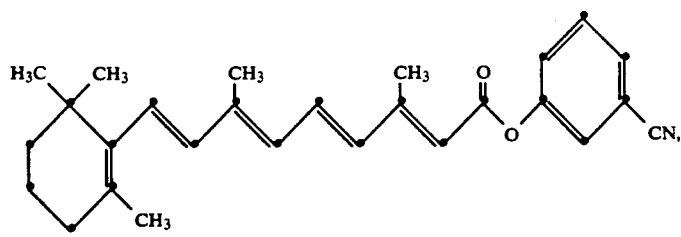
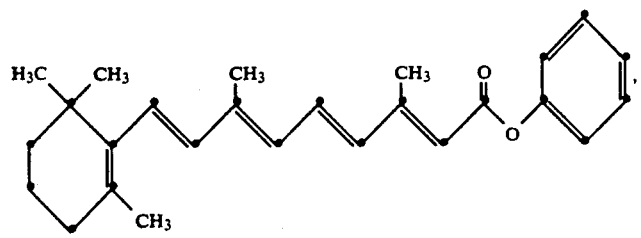

-continued
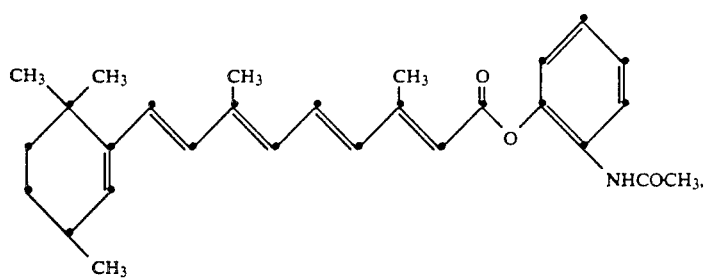
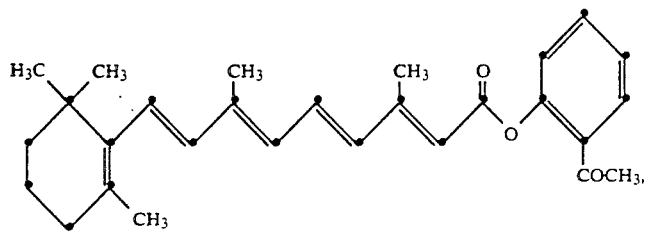
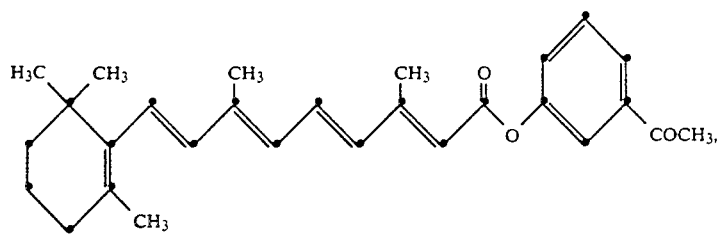
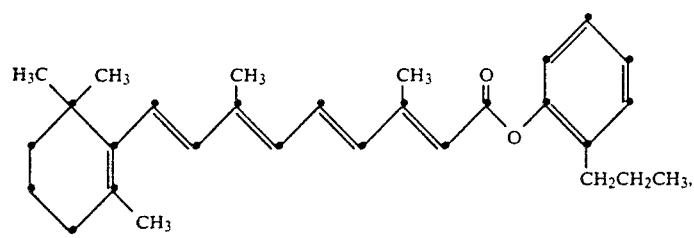
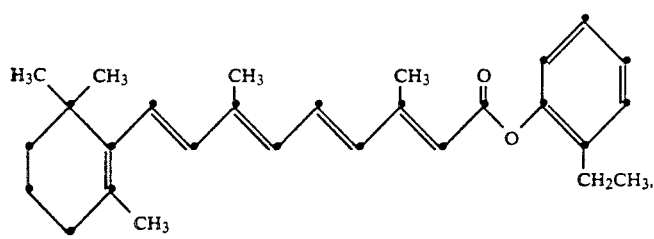
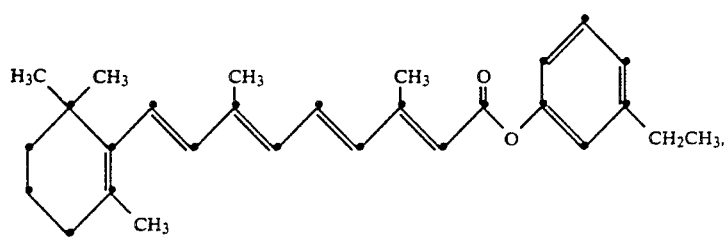

-continued
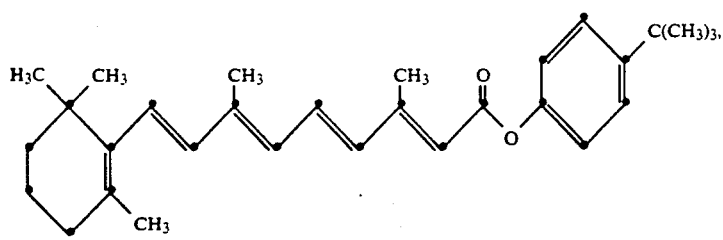
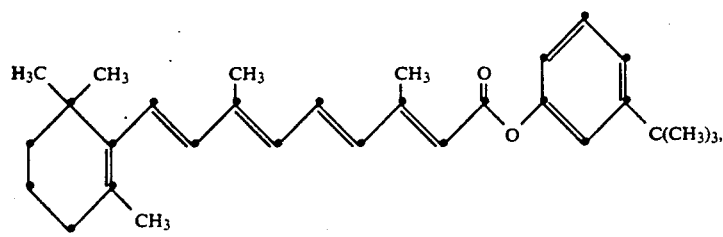
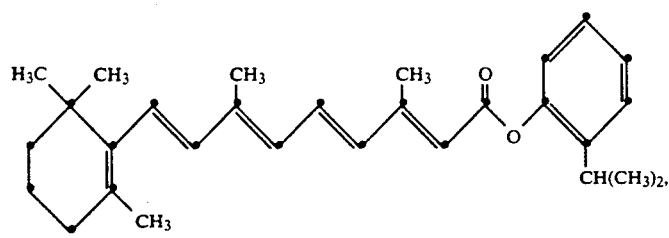
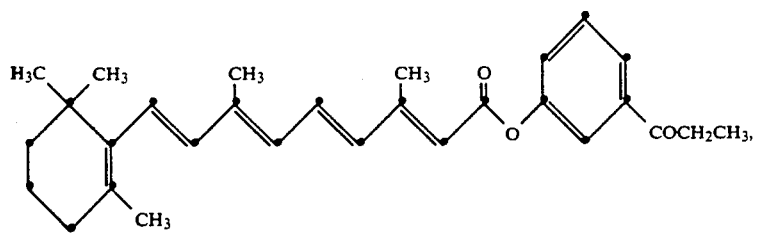
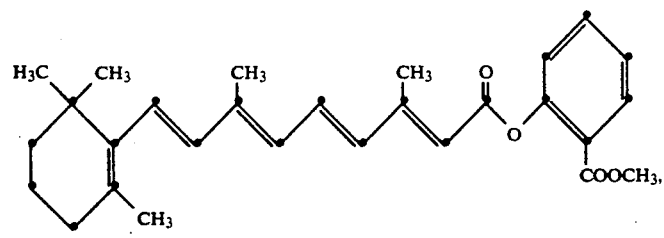
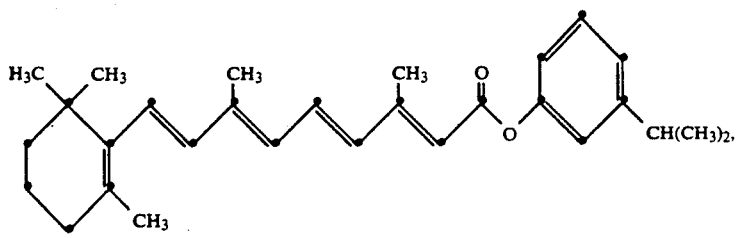

-continued
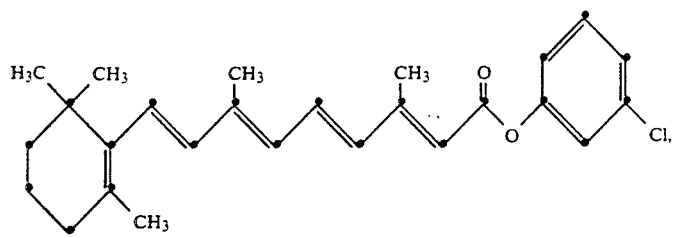
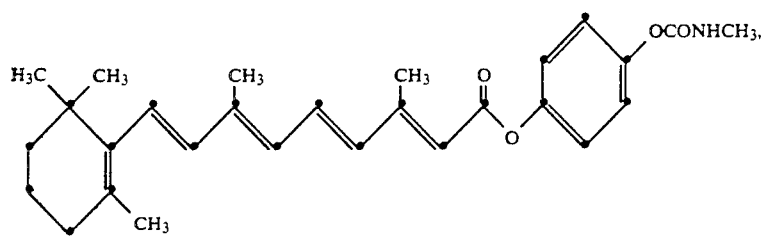
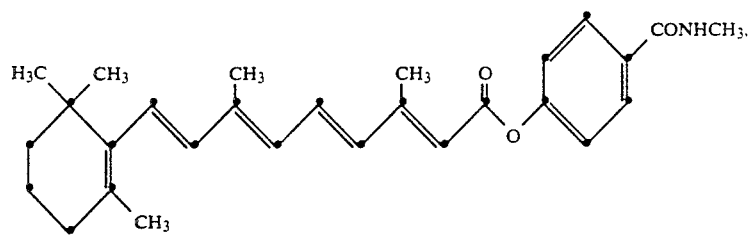
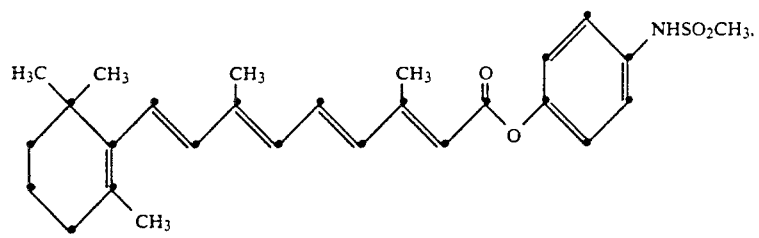
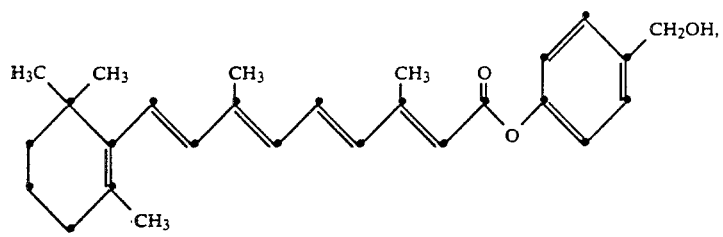
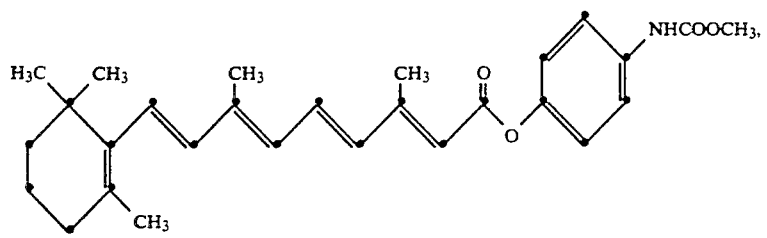

-continued

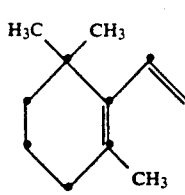

13. A compound having the structure:

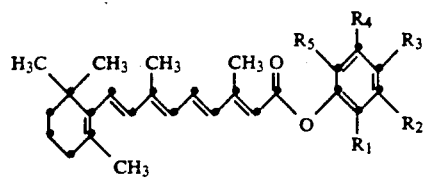

wherein
any three of $R_1$, $R_2$, $R_3$, $R_4$ and $R_5$ are independently selected from the group consisting of H, Cl, $NO_2$, CN, $OR_6$, $NR_6C(=S)NR_7R_8$, $SO_2NR_6R_7$, $CH(CH_3)COOH$, $OCONR_6R_7$, $NR_6COONR_7$, $R_9OR_6$, $NR_6SO_2R_7$, $Si(CH_3)_3$, $NR_6CONR_7R_8$, $NR_6COR_7$, with the proviso that where $R_2$, $R_3$ or $R_4$ is $NHCOR_7$, and $R_1$ and $R_2$ are hydrogen, $R_7$ cannot be methyl, straight or branched alkyl of 1 to 10 carbon atoms, with the proviso where $R_1$ is alkyl, the alkyl cannot contain an acetal, $COOR_6$, with the proviso that where $R_1$ is $COOR_6$, $R_6$ is not hydrogen or methyl, and that where $R_3$ is $COOR_6$, $R_6$ is not ethyl, $NR_6R_7$, with the proviso that where $R_1$ or $R_3$ are $NR_6R_7$, $R_6$ and $R_7$ are not both hydrogen, $CONR_6R_7$, with the proviso that where $R_1$ is $CONR_6R_7$, $R_6$ and $R_7$ are not both hydrogen, and $COR_6$, with the proviso that where $R_3$ is $COR_6$, $R_6$ is not hydrogen, $R_3$ together with $R_4$ forms a benzo ring or taken together with $R_2$ forms a benzo or tetrahydrobenzo ring or together with $R_2$ and $R_1$ forms a:

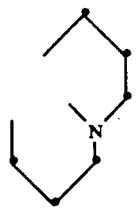

moiety or together with $R_2$ forms a

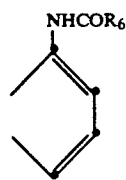

moiety or $R_2$ together with $R_1$ forms a benzo ring

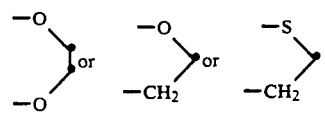

or
$R_1$ is independently selected from the group consisting of

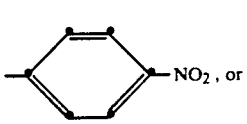

moiety,
$R_6$, $R_7$ and $R_8$ are independently selected from the group consisting of straight or branched alkyl containing from 1 to 10 carbon atoms, aryl containing from 6 to 10 carbon atoms and hydrogen, and
$R_9$ is alkylene of 1 to 6 carbon atoms,
and iron carbonyl complexes thereof.

14. The compound of claim 13 wherein $R_2$ and $R_3$ are independently selected from the groups consisting of $NR_6COR_7$, $CONR_6R_7$, $SO_2NR_6R_7$, $OCONR_6R_7$, $NR_6COOR_7$, $NR_6CONR_7R_8$, $NR_6SO_2R_7$ and $NR_6C(=S)NR_7R_8$.

15. A compound having the structure:

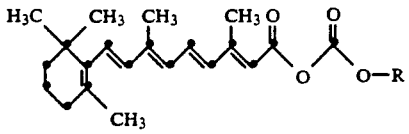

wherein
R is

—$C_2H_5$, —$CH_2CF_3$, —CH=$CH_2$, 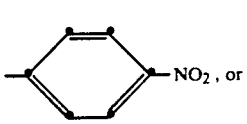

-continued
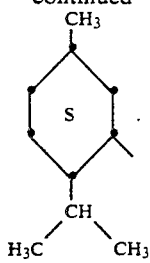
16. A compound of claim 13 selected from the group consisting of the following structures:
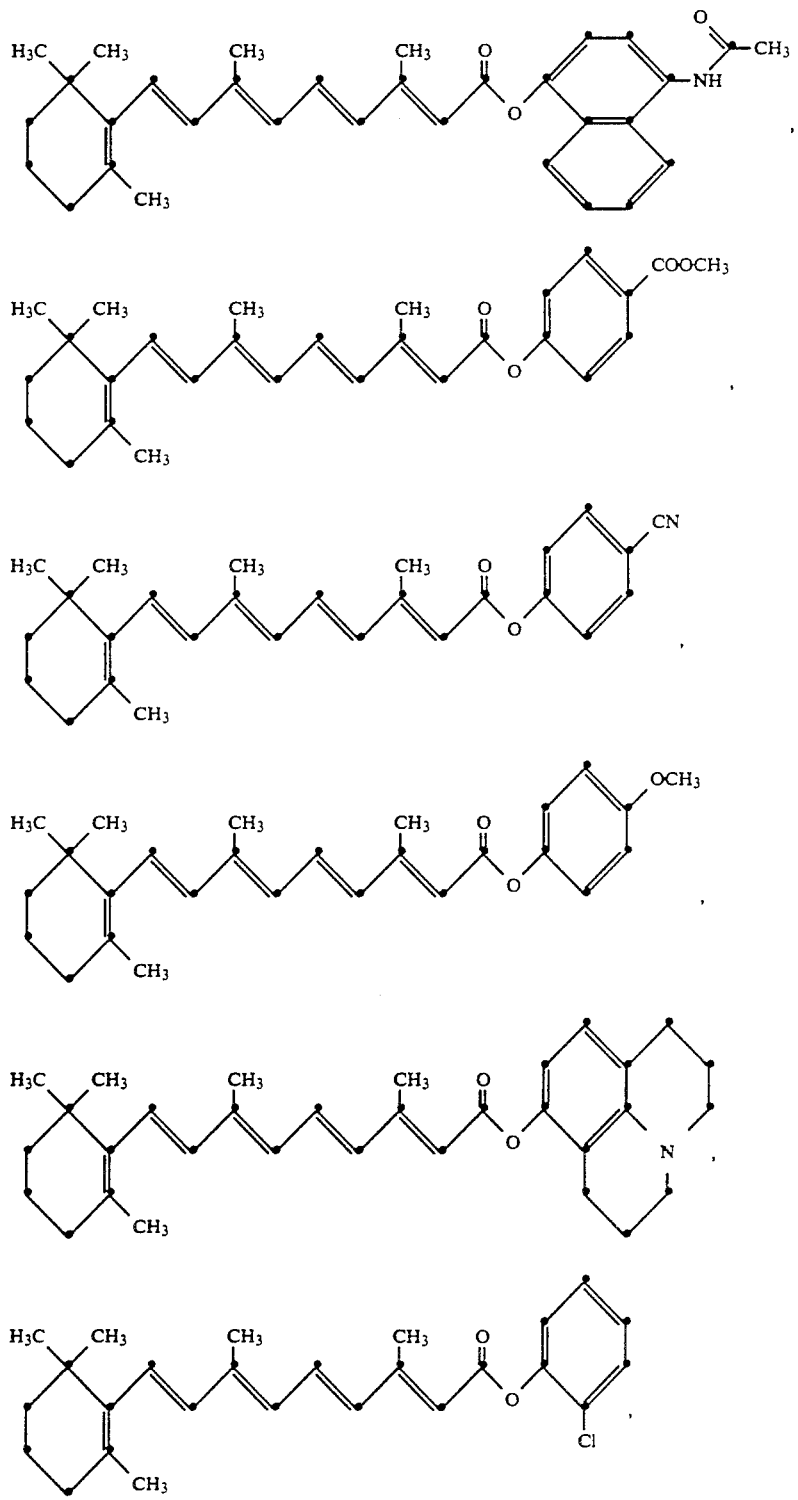

-continued
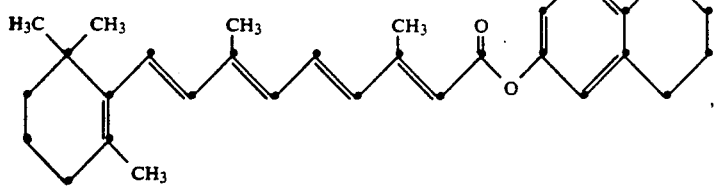
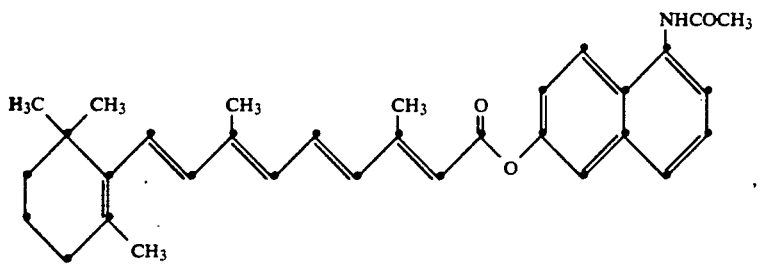
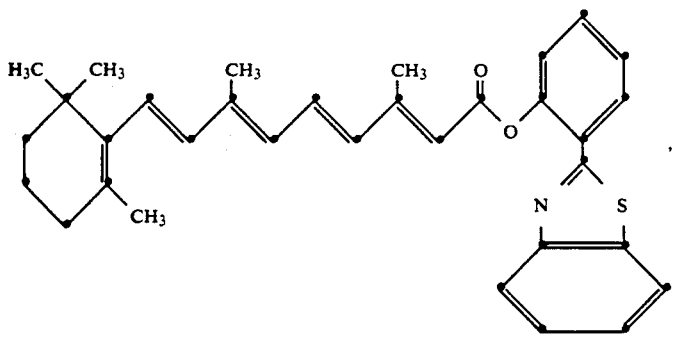
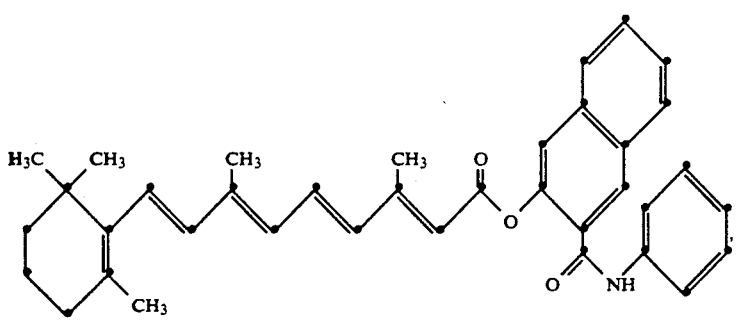
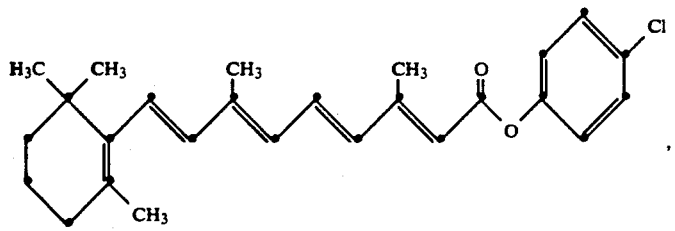
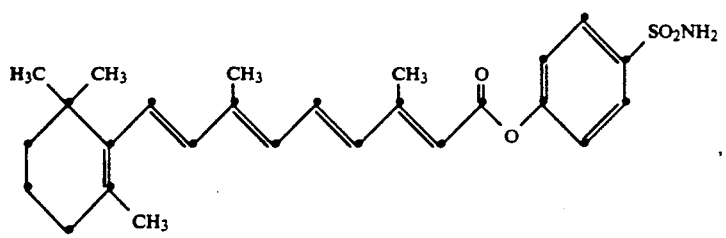

-continued
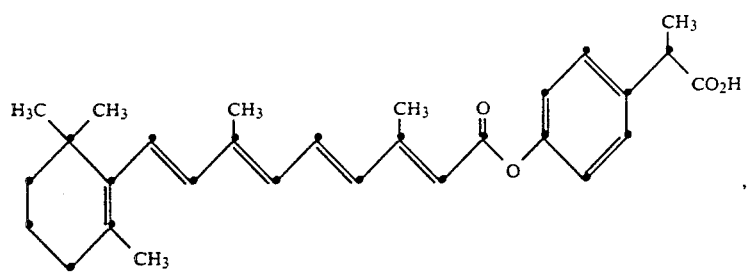
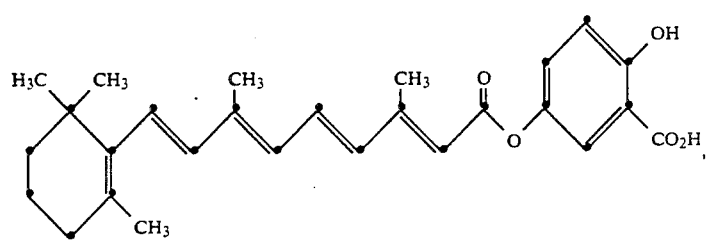
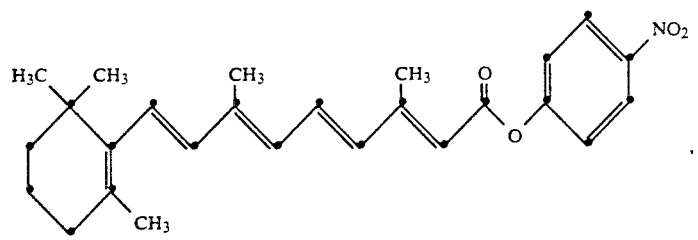
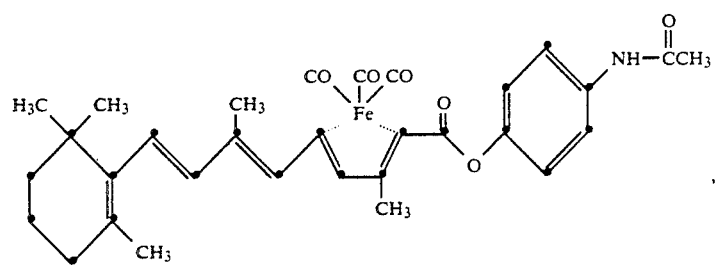
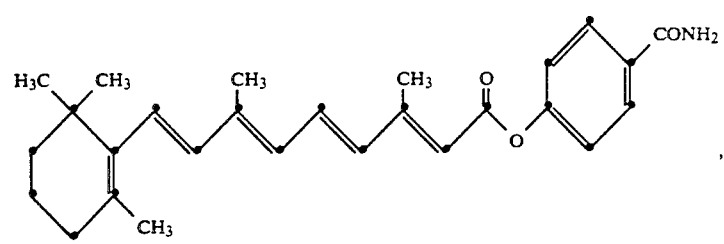
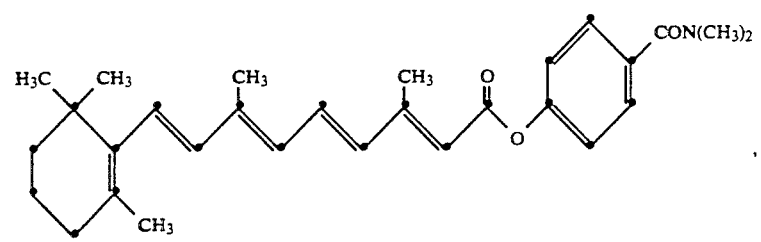

-continued
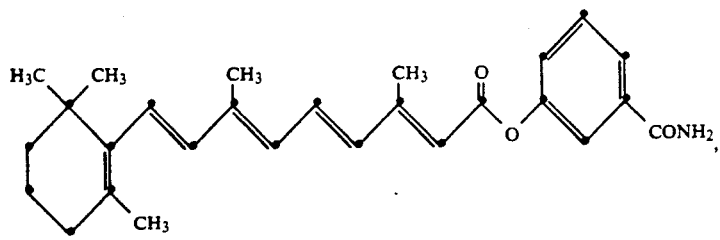,
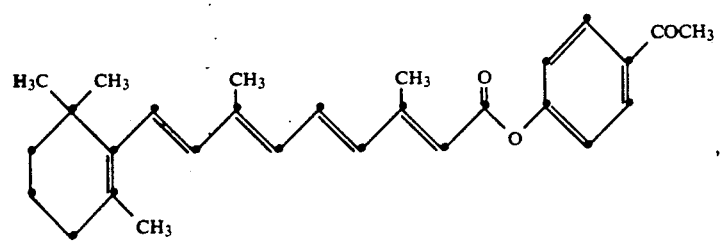,
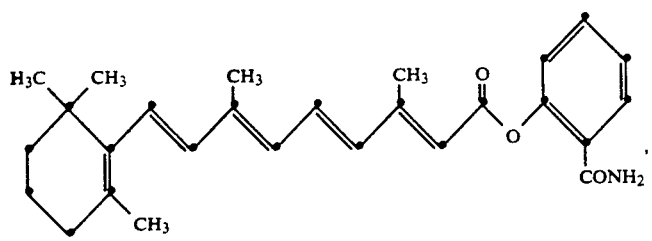,
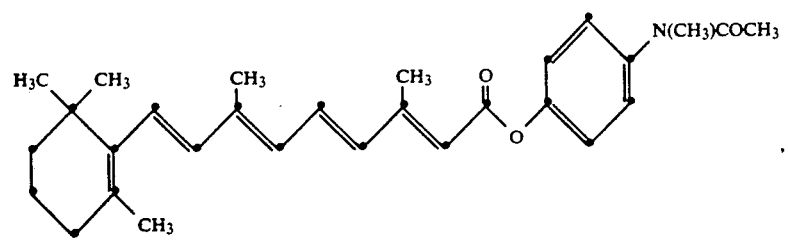,
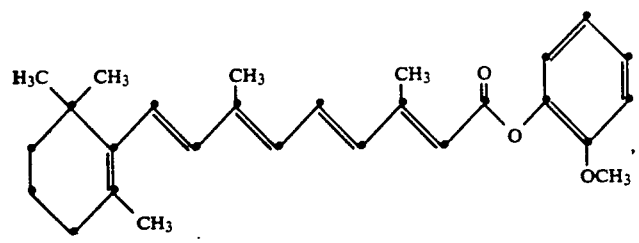,
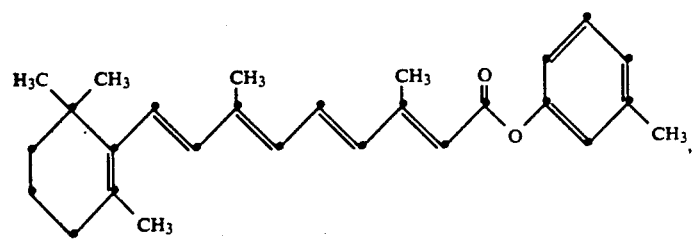, -continued
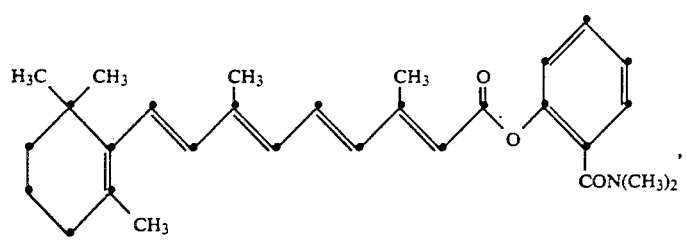
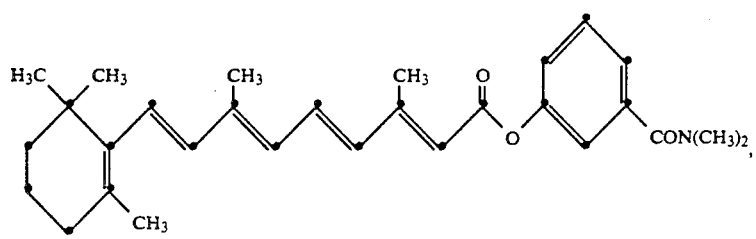
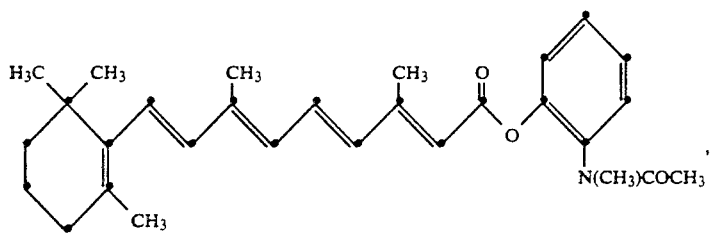
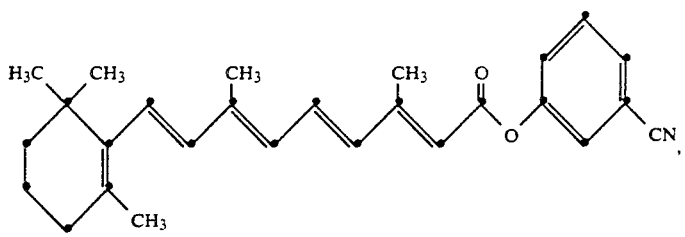
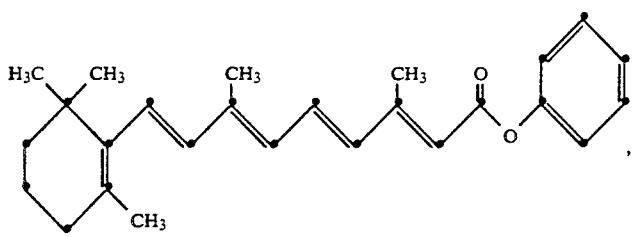
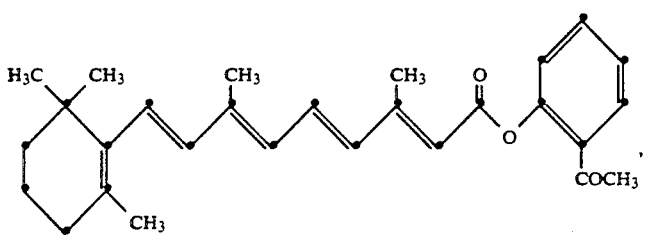

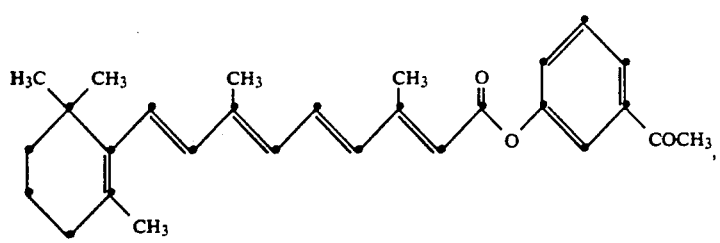,
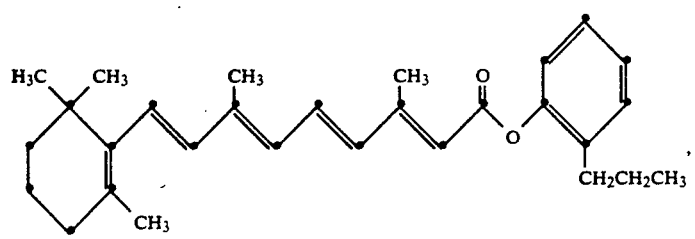,
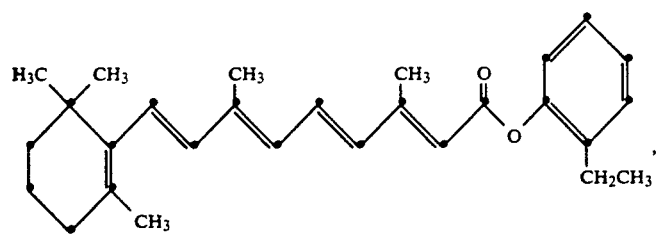,
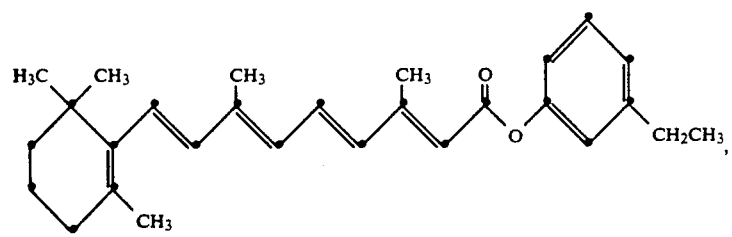,
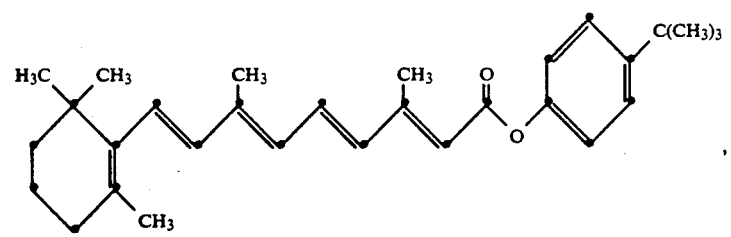,
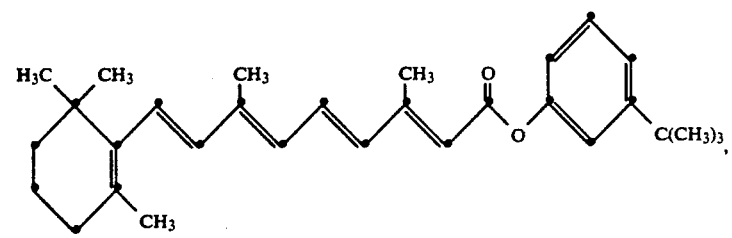,

-continued
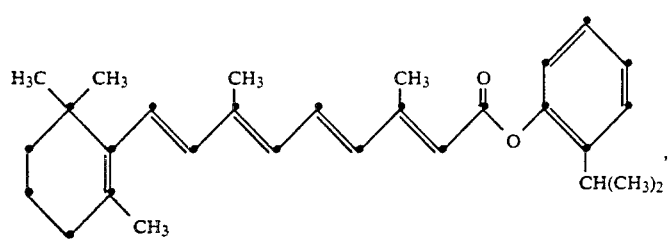
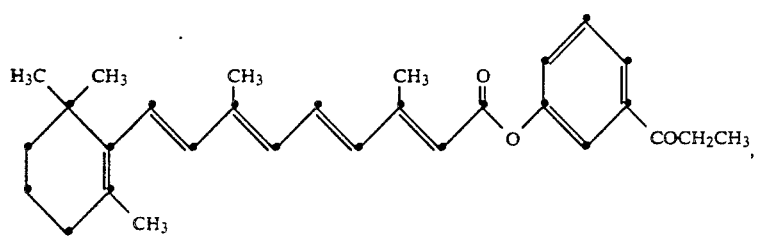
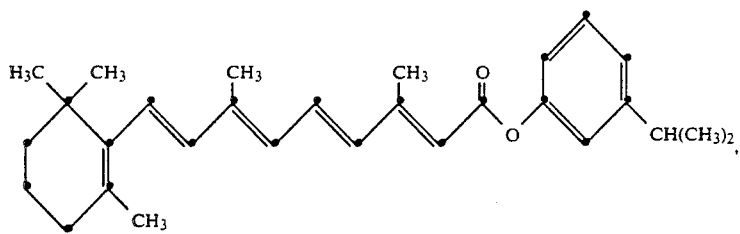
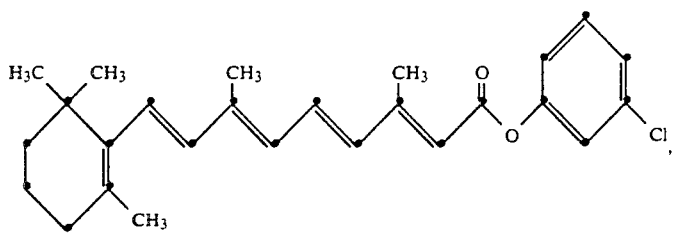
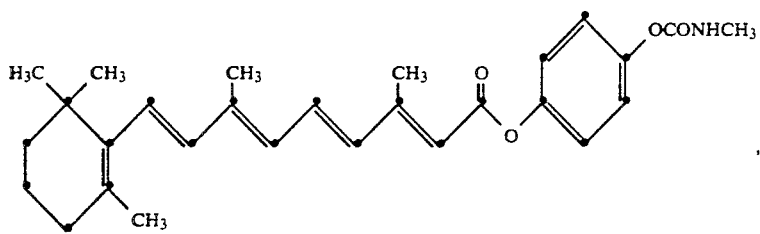
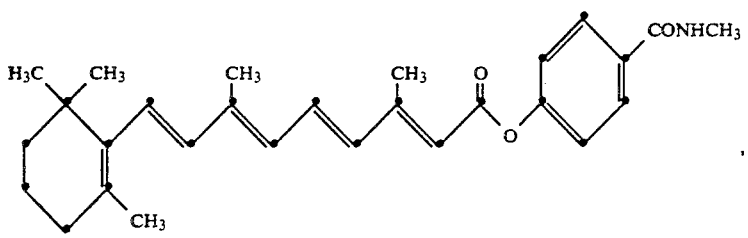

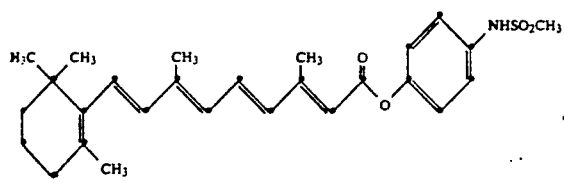
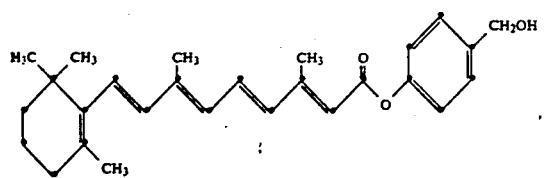
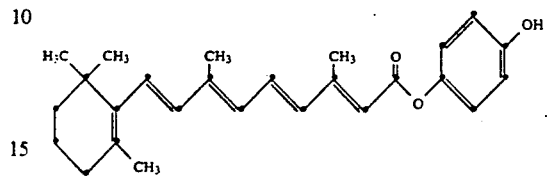
* * * * *